United States Patent
Anker et al.

(10) Patent No.: US 10,667,745 B2
(45) Date of Patent: Jun. 2, 2020

(54) RADIOGRAPHIC DISCERNABLE SENSORS AND ORTHOPEDIC APPLICATIONS FOR SAME

(71) Applicant: Clemson University, Clemson, SC (US)

(72) Inventors: Jeffrey Anker, Greenville, SC (US); Caleb Behrend, Pittsford, NY (US); John DesJardins, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 153 days.

(21) Appl. No.: 15/751,623

(22) PCT Filed: Aug. 12, 2016

(86) PCT No.: PCT/US2016/046707
§ 371 (c)(1),
(2) Date: Feb. 9, 2018

(87) PCT Pub. No.: WO2017/027782
PCT Pub. Date: Feb. 16, 2017

(65) Prior Publication Data
US 2018/0228428 A1    Aug. 16, 2018

Related U.S. Application Data

(60) Provisional application No. 62/204,111, filed on Aug. 12, 2015.

(51) Int. Cl.
*A61B 5/00* (2006.01)
*G01L 1/24* (2006.01)
(Continued)

(52) U.S. Cl.
CPC .......... *A61B 5/4504* (2013.01); *A61B 5/0031* (2013.01); *A61B 5/1071* (2013.01);
(Continued)

(58) Field of Classification Search
CPC .. A61F 5/00; A61F 5/45; A61F 5/4509; A61F 5/1127; A61F 6/00
See application file for complete search history.

(56) References Cited

U.S. PATENT DOCUMENTS

| 4,822,336 A | 4/1989 | Ditraglia |
| 5,483,571 A | 1/1996 | Madaras |
| (Continued) | | |

OTHER PUBLICATIONS

Augat, et al., Biomechanical methods for the assessment of fracture repair. *Injury* 45, (2014), S32.
(Continued)

*Primary Examiner* — Jason-Dennis N Stewart
(74) *Attorney, Agent, or Firm* — Dority & Manning, P.A.

(57) ABSTRACT

Implantable sensors for determining bone health are described that can be utilized in conjunction with orthopedic implants. The sensors can include passive strain gauges or passive chemical sensors that can be read by radiographic imaging techniques. Sensors can be affixed to implantable support devices so as to non-invasively monitor the effect of load on the implant for instance to provide a quantitative assessment of when a fracture is sufficiently healed to allow safe weight-bearing upon the limb. Alternatively, sensors can monitor the health of a local implant area, for instance to monitor the implant area of early stage infection or healing of a fusion procedure.

21 Claims, 16 Drawing Sheets

(51) Int. Cl.
- G01L 1/25 (2006.01)
- A61B 6/12 (2006.01)
- A61B 6/00 (2006.01)
- A61B 5/107 (2006.01)
- A61B 17/72 (2006.01)
- A61B 17/80 (2006.01)
- G01L 19/08 (2006.01)

(52) U.S. Cl.
CPC ............... *A61B 6/12* (2013.01); *A61B 6/505* (2013.01); *A61B 17/72* (2013.01); *A61B 17/80* (2013.01); *G01L 1/24* (2013.01); *G01L 1/25* (2013.01); *G01L 19/086* (2013.01)

(56) References Cited

U.S. PATENT DOCUMENTS

| | | | |
|---|---|---|---|
| 5,935,084 | A | 8/1999 | Southworth |
| 6,751,491 | B2 | 6/2004 | Lew et al. |
| 7,479,112 | B2 | 1/2009 | Sweeney et al. |
| 8,697,029 | B2 | 4/2014 | Anker et al. |
| 9,179,865 | B2 | 11/2015 | Anker et al. |
| 2004/0058458 | A1 | 3/2004 | Anker et al. |
| 2006/0008924 | A1 | 1/2006 | Anker et al. |
| 2014/0046191 | A1 | 2/2014 | Anker et al. |
| 2015/0362500 | A1 | 12/2015 | Anker et al. |

OTHER PUBLICATIONS

Betts, et al., Mechanical regulation of bone regeneration: theories, models, and experiments. *Frontiers in Endocrinology* 5, (2014), 57-70.
Blokhuis, et al., The reliability of plain radiography in experimental fracture healing. *Skeletal Radiology* 30, (2001), 151.
Borrelli, et al., Assessment of articular fragment displacement in acetabular fractures: a comparison of computerized tomography and plain radiographs. *Journal of Orthopaedic Trauma* 16, (2002) 449. (Abstract only).
Bottlang, et al., The bottleneck of evidence-based fracture care. *Injury* 45, (2014), S1.
Bourgois, et al., Measurement of the stiffness of fracture callus in vivo. A theoretical study. *Journal of Biomechanics* 5, (1972), 85. (Abstract only).
Brunner, et al., Fatigue fracture of bone plates, *Injury* 11, (1980), 203. (Abstract only).
Chehade, et al., Differentially Loaded Radiostereometric Analysis to Monitor Fracture Stiffness: A Feasibility Study. *Clinical Orthopaedics and Related Research®* 467, (2009), 1839.
Claes, et al., Monitoring the Mechanical Properties of Heating Bone. *Clinical Orthopaedics and Related Research®* 467, (2009), 1964.
Claes, et al., Monitoring and healing analysis of 100 tibial shaft fractures. *Langenbeck's Archives of Surgery* 387, (2002), 146. (Abstract only).
Cunningham, et al., The measurement of stiffness of fractures treated with external fixation. *Engineering in Medicine* 16, (1987), 229.
D'Lima, et al., Implantable sensor technology: measuring bone and joint biomechanics of daily life in vivo. *Arthritis Research & Therapy* 15, (2013), 203.
Ehrlich, et al., Engineering Approaches for the Detection and Control of Orthopaedic Biofilm Infections. *Clin. Orthop. Relat. Res.* 437, (2005), 59-66.
Floerkemeier, et al., Comparison of various types of stiffness as predictors of the load-bearing cipacity of callus tissue. *Journal of Bone & Joint Surgery*, British vol. 87, (2005), 1694.
Goldstein, et al., When is a spine fused? *Injury* 42, (2011), 306. (Abstract only).
Grasa, et al., Monitoring m vivo load transmission through an external fixator. *Annals of Biomedical Engineering*, 38, (2010), 605-612.
Gruskay, et al., Methods of evaluating lumbar and cervical fusion. *The Spine Journal* 14(3), (2014), 431-539.
Hak, et al., Delayed union and nonunions: Epidemiology, clinical issues, and financial aspects. *Injury* 45, (2014), S3.
Hammer, et al., Evaluation of fracture stability: a mechanical simulator for assessment of clinical judgement *Acta Orthopaedica* 55, (1984), 330.
Henry, et al., Studies on the mechanical properties of healing experimental fractures. *Proceedings of the Royal Society of Medicine* 61, (1968), 902.
Jagodzinski, et al., Effect of mechanical stability on fracture healing—an update. *Injury* 38, (2007), S3.
Johnson, et al., Operation Iraqi Freedom: the Landstuhl Regional Medical Center experience. *The Journal of Foot and Ankle Surgery* 44, (2005), 177.
Lindeque, et al., A biomechanical comparison of three different lateral tibia locking plates. *Orthopedics* 33, (2010), 18.
Melik, et al., Bio-implantable passive on-chip RF-MEMS strain sensing resonators for orthopaedic applications. *Journal of Micromechanics and Microengineering* 18, (2008), 115017.
Mody, et al., Infectious Complications of Damage Control Orthopedics in War Trauma. *The Journal of Trauma: Injury, Infection, and Critical Care* 67, (2009), 758.
Naderi, et al., Probabilistic simulation of fatigue damage and life scatter of metallic components. *International Journal of Plasticity* 43, (2013), 101.
Nakatsuchi, et al., The vibrational mode of the tibia and assessment of bone union in experimental fracture healing using the impulse response method. *Medical Engineering & Physics* 18, (1996), 575.
Owens, et al., Combat wounds in operation Iraqi Freedom and operation Enduring Freedom. *Journal of Trauma and Acute Care Surgery* 64, (2008), 295.
Panjabi, et al., Correlations of radiographic analysis of healing fractures with strength: a statistical analysis of experimental osteotomies. *Journal of Orthopaedic Research* 3, (1985) 212, (Abstract only).
Papakostidis, et al., Prevalence of complications of open tibial shaft fractures stratified as per the Gustilo-Anderson classification. *Injury* 42, (2011), 1408.
Perren, S., Physical and biological aspects of fracture healing with special reference to internal fixation. *Clinical Orthopaedics and Related Research* 138, (1979), 175.
Richardson, et al., Measuring stiffness can define healing of tibial fractures. *Journal of Bone & Joint Surgery*, British vol. 76, (1994), 389.
Schwarzbach, et al. Clinical Value of [18-F] Fluorodeoxyglucose Positron Emission 23 Tomography Imaging in Soft Tissue Sarcomas. *Annals of Surgery*. 231(3), (2000), 380-386.
Seide, et al., Telemetric assessment of bone healing with an instrumented internal fixator A preliminary study. *Journal of Bone & Joint Surgery*, British vol. 94, (2012), 398.
Song, et al., Dynamic Radiographic Criteria for Detecting Pseudarthrosis Following Anterier Cervical Arthrodesis. *The Journal of Bone & Joint Surgery* 96, (2014), 557-563.
Steiner, et al., Numerical simulation of callus healing for optimization of fracture fixation stiffness. *Plos One* 9(7), e101370, (2014), 1-11.
Stoffel, et al., Functional load of plates in fracture fixation in vivo and its correlate in bone healing. *Injury* 31, (2000), 37.
Tan, et al., Implantable Biosensors for Real-time Strain and Pressure Monitoring. *Sensors* 8, (2008), 6396.
Umbrecht, et al., Wireless implantable passive strain sensor: design, fabrication and characterization. *Journal of Micromechanics and Microengineering* 20, (2010), 085005-085018.
Wade, et al., Outcome in fracture healing: A review. *Injury, Int. J. Care Injured* 32 (2001) 109-114.
Wang, et al., X-Ray Excited Luminescence Chemical Imaging of Bacterial Growth on Surfaces Implanted in Tissue. *Advanced Healthcare Materials* 4(6), (2015), 903-910.

(56) References Cited

OTHER PUBLICATIONS

Wong, et al., Review of techniques for monitoring the healing fracture of bones for implementation in an internally fixated pelvis. *Medical Engineering & Physics* 34, (2012), 140.

Xu, et al., Biomechanical comparison of gourd-shaped LCP versus LCP for fixation of comminuted tibial shaft fracture. *Journal of Huazhong University of Science and Technology [Medical Sciences]* 33, (2013), 250.

Zimmerli, W., Prosthetic-joint-associated infections. *Best Practice & Research Clinical Rheumatology*, 20(6), (2006), 1045-1063.

PCT International Search Report & Written Opinion, PCT/US16/046707. (dated 2016).

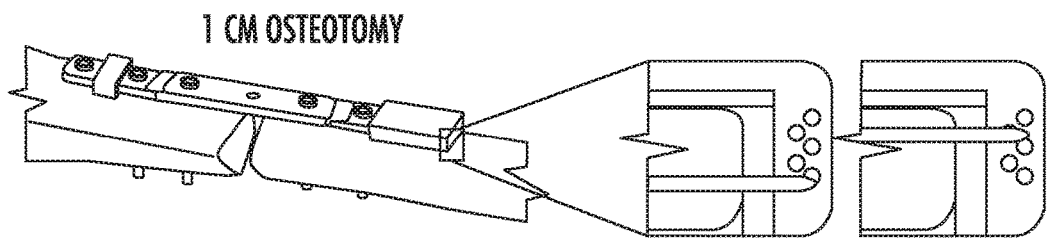
FIG. 19A 1 CM OSTEOTOMY
FIG. 19B 0 N LOAD  400 N LOAD
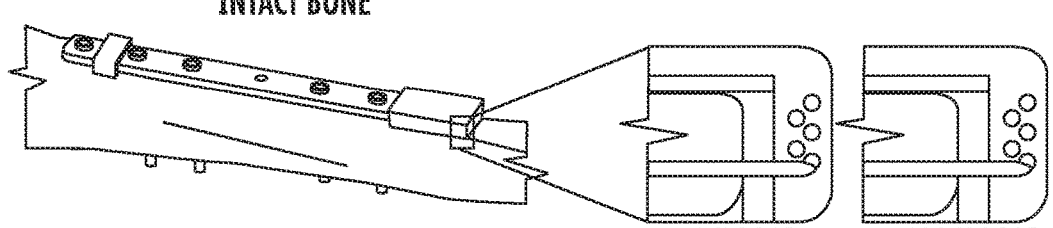
FIG. 19C INTACT BONE
FIG. 19D 0 N LOAD  400 N LOAD
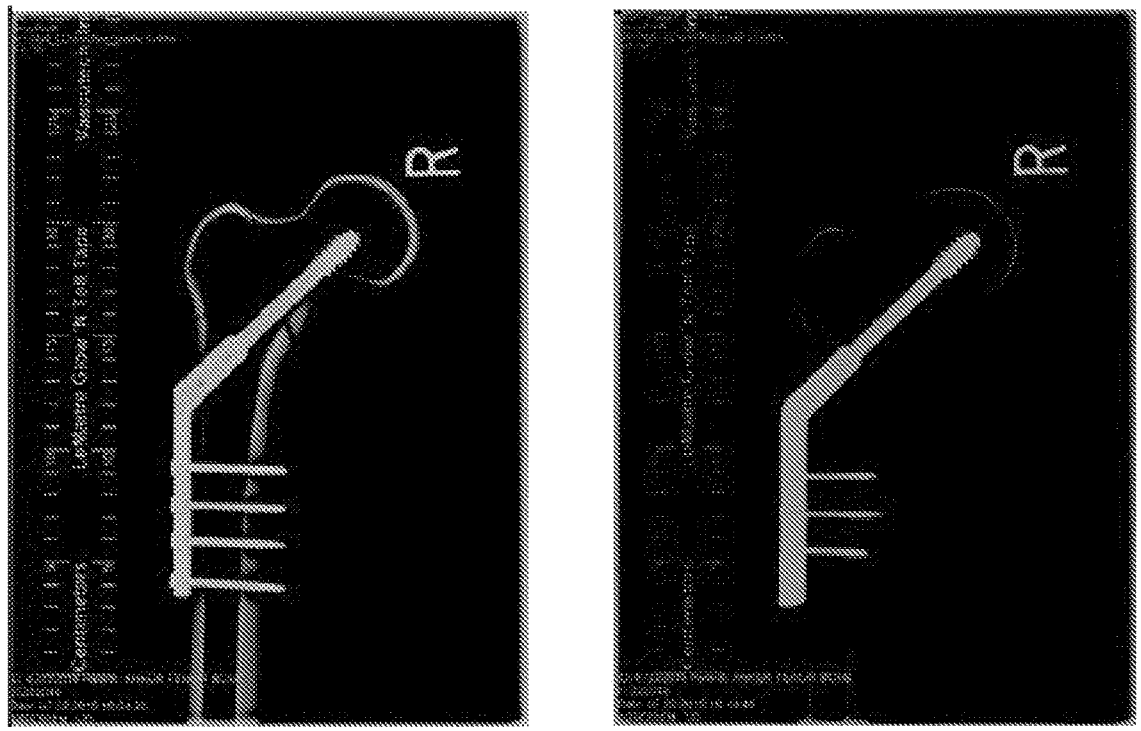
FIG. 20

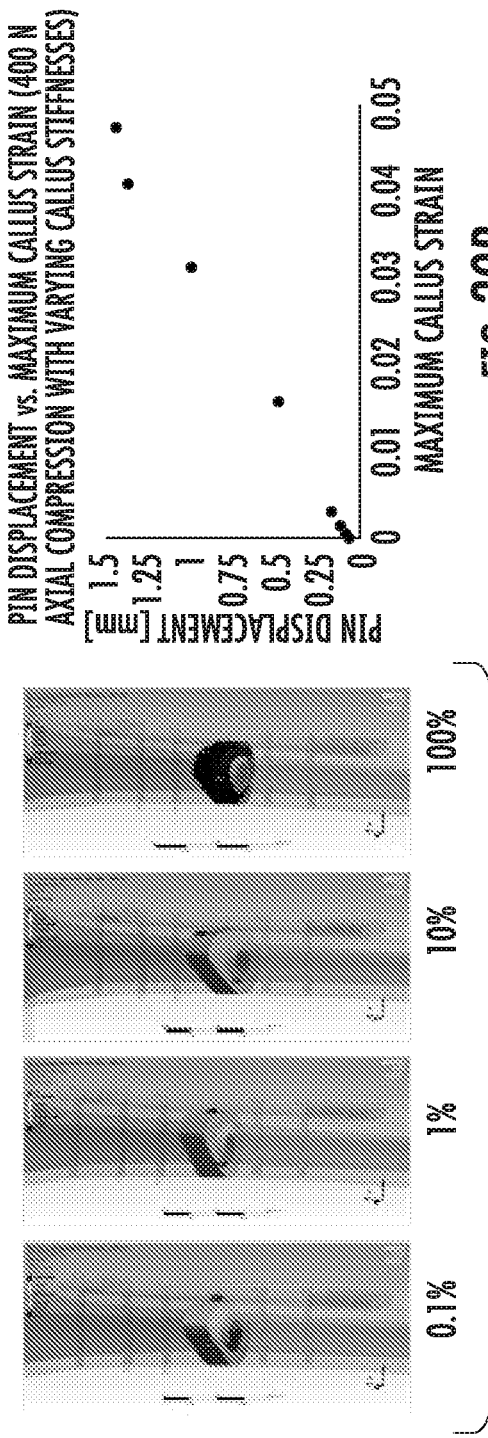
FIG. 30A
FIG. 30B
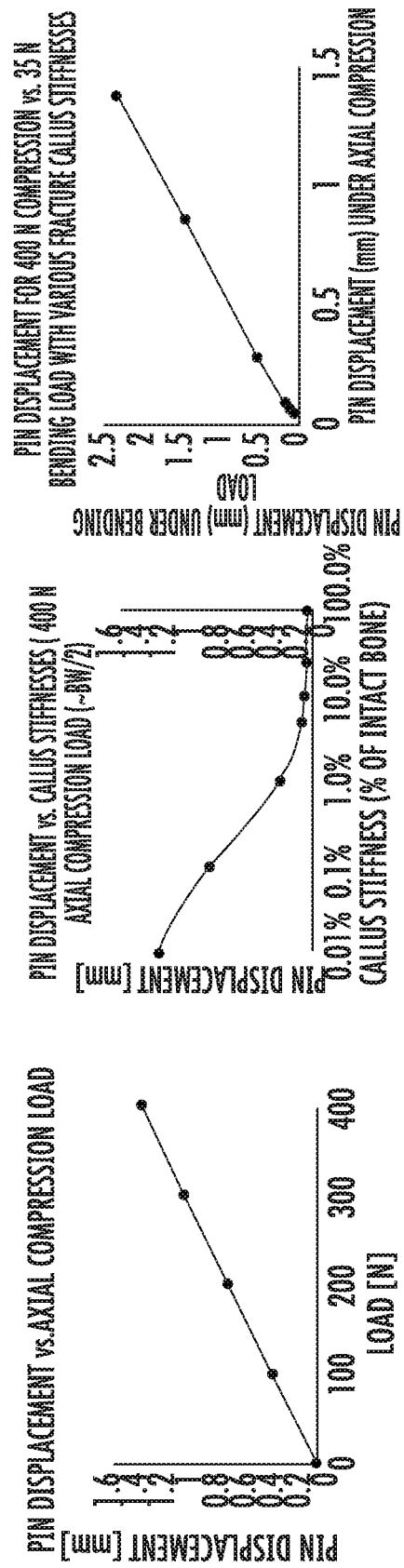
FIG. 31A
FIG. 31B
FIG. 31C

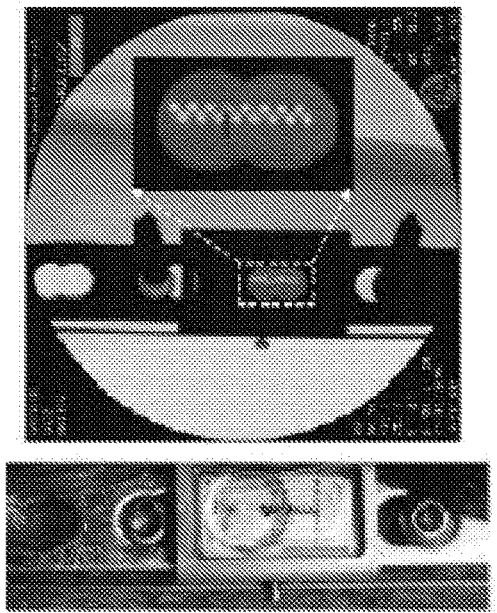
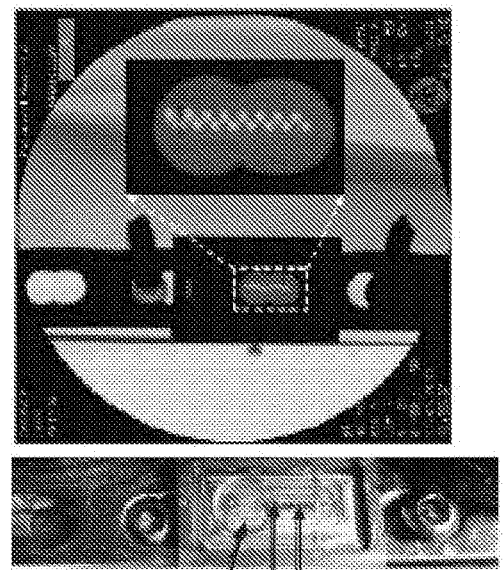
pH-INDICATING GEL
TUNGSTEN ROD IN GEL
SCALE HOLES
FIG. 32
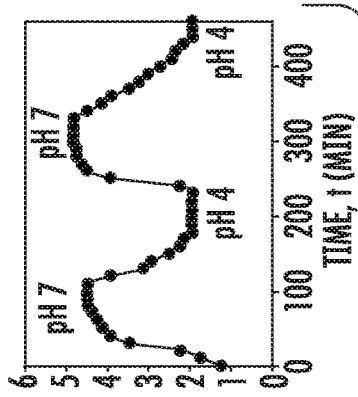
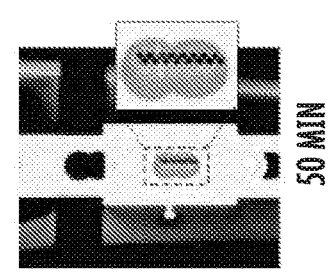
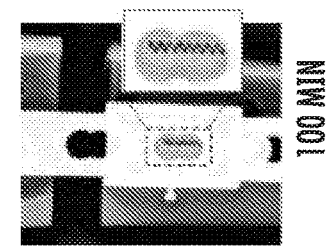
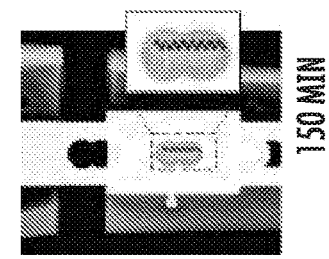
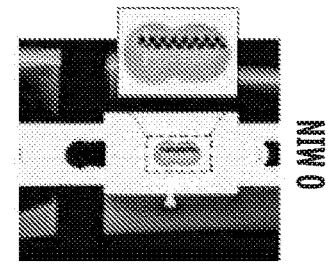
FIG. 33

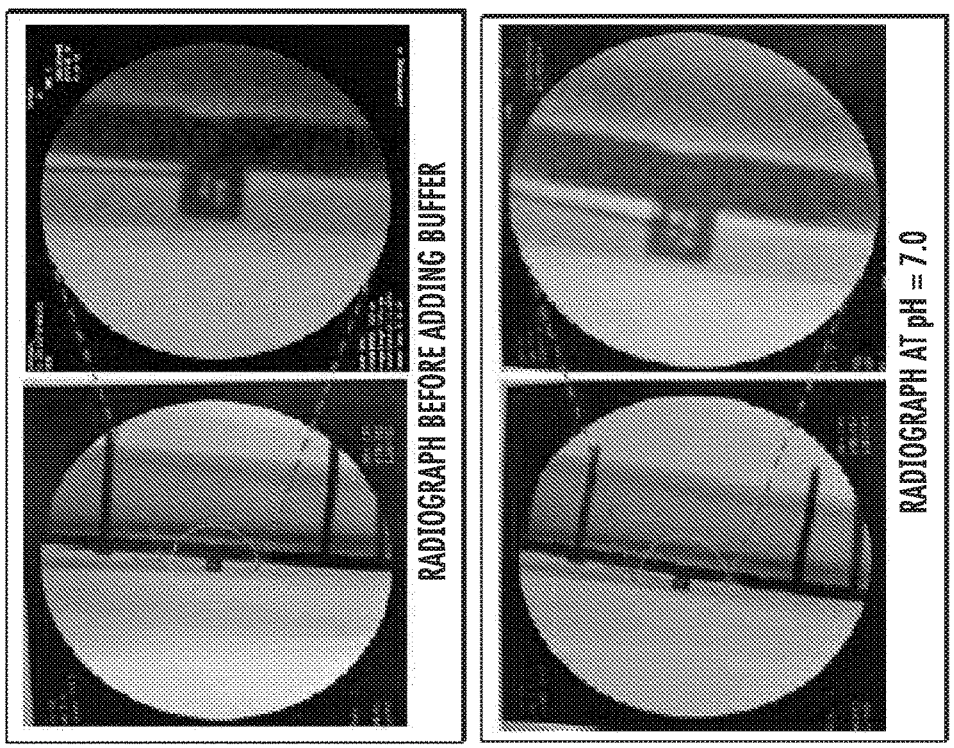
FIG. 34C
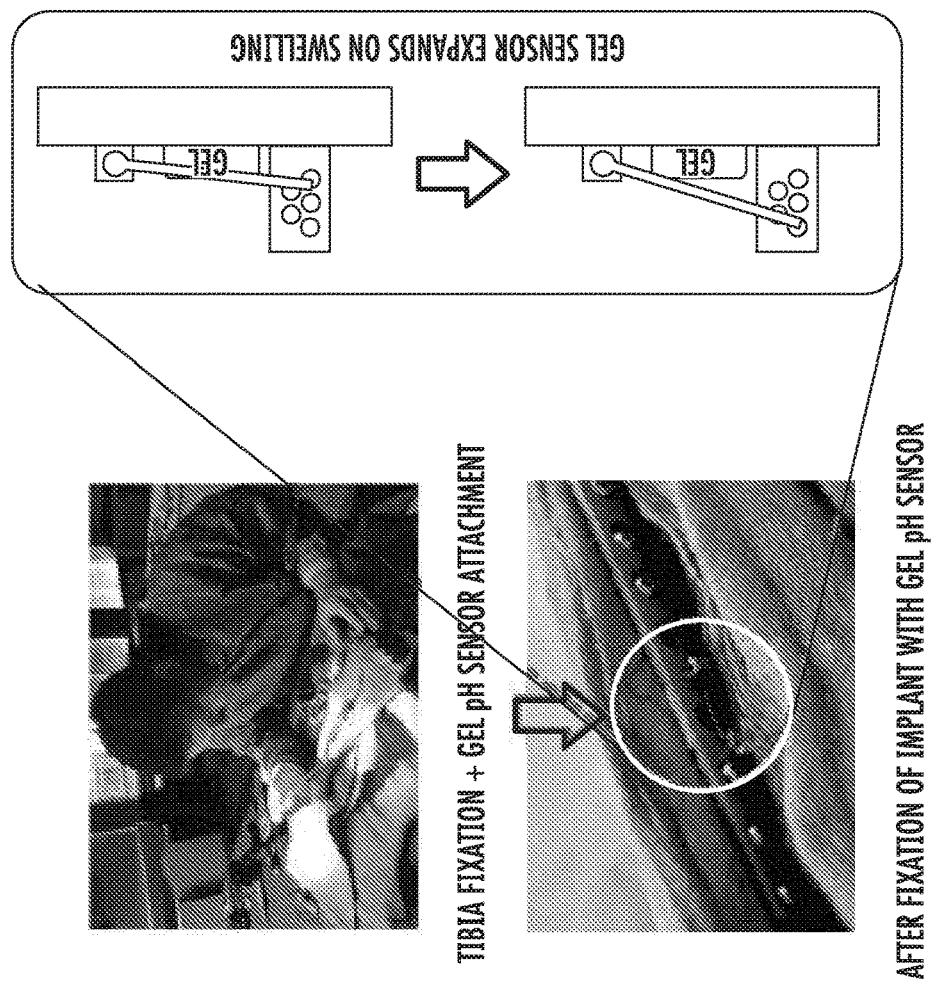
FIG. 34B
FIG. 34A

RADIOGRAPHIC DISCERNABLE SENSORS AND ORTHOPEDIC APPLICATIONS FOR SAME

CROSS REFERENCE TO RELATED APPLICATION

This application claims filing benefit of U.S. Provisional Patent Application Ser. No. 62/204,111 having a filing date of Aug. 12, 2015, which is incorporated herein by reference in its entirety.

STATEMENT REGARDING FEDERALLY SPONSORED RESEARCH OR DEVELOPMENT

This invention was made with government support under Grant No. GM103444 awarded by the National Institutes of Health. The government has certain rights in the invention.

BACKGROUND

Over 28 million musculoskeletal injuries are treated annually in the U.S. including 2 million fracture fixation surgeries. Of these, tibia fractures are the most common long bone fracture. Unfortunately, such fractures are frequently associated with complications (delayed union, non-union, and infection), particularly for severe trauma such as is often sustained in combat. For instance, non-union is a significant complication (approximately 100,000 injuries, 5% of all fixation surgeries in the U.S. go on to non-union), with even higher rates for severe trauma. Infection at the site of orthopedic surgery is an on-going issue and, while the incidence has been reduced due to improvements in both surgical and post-operative procedures, its prevalence is still unacceptably high. Such complications can lead to long-term or even permanent disability or death and are responsible for significant direct and indirect health care costs.

While a variety of supporting implants and adjunct therapies are available to care givers, a crucial issue leading to complication is the inability to directly evaluate health and healing of the local area. Physicians routinely acquire X-ray images as part of diagnosis and evaluation and while these images can show the hardware and fracture callus, they do not measure mechanical properties of the fracture and cannot detect early-stage infection. 3-dimensional CT images are better at indicating bone density and determining if union has occurred, but are expensive, expose the patient to significant radiation doses (typically around 300x more than a standard X-ray), and are imperfect, especially when allografts are used. For some fracture types, dynamic X-ray images can be acquired to measure bone motion with and without external load in order to assess fracture stability. In practice however this is highly challenging. For example, even in spine fusion, where spinal processes are clearly evident and can move significantly, it has been determined that inter-observer variation of spinous process movement can be about 1.5 mm, with differences as large as 3.5 mm, compared to a recommended bone fusion cutoff criteria of less than 1 mm.

When considering localized infection, external visualization techniques provide little or no clues, particular in early stages of infection. Unfortunately, infection at orthopedic trauma sites are generally not diagnosed until after the infection has spread and symptoms have become systemic.

The lack of widely applicable tests to assess bone health such as load bearing state and early stage infection presents a major challenge for physicians and patients. Infection at implant sites can require additional surgery or even become life-threatening when diagnosis is delayed. Weight bearing before the fracture callus is sufficiently strong carries risk of re-fracture and/or hardware failure. On the other hand, unnecessary delay in weight bearing can hamper rehabilitation and is highly costly in terms of lost days of activity. Studies have shown that when the fractured bone has at least 25% of the bending stiffness of intact bone, weight bearing rarely leads to re-fracture or hardware failure. For externally fixed devices, percutaneous pins can be directly loaded to assess stiffness. When testing is carried out and this 25% threshold is used, the majority of patients begin weight bearing an average of 2.3 weeks earlier than average. Load testing on externally fixated devices can likewise identify patients with delayed and non-union for weight bearing restrictions and additional interventions.

Most orthopedic surgeries involve internal fixation, which require either a percutaneously connected gauge or remote measurements to assess load bearing capabilities during healing. A percutaneously connected strain gauge is impractical for patients and presents a number of safety challenges. A variety of remote interrogation methods based upon implanted wireless devices, ultrasound, vibrational analysis, and other approaches have been examined for non-invasive measurement of strain on orthopedic implants, but these generally require significant development as well as equipment and/or expertise currently unavailable to most care givers.

What are needed in the art are passive implantable sensors for use in conjunction with orthopedic implants that can be easily read by conventional non-invasive methods to assess local conditions and bone health at the local site. In particular, what are needed are passive sensors capable of assessing strain under load and/or early stage signs of infection and thereby to determine a current state of bone health. For instance, a passive sensor locatable on bone fixation devices that can assess health and healing in the local area of an orthopedic implant by use of conventional radiography methods would be of great benefit.

SUMMARY

According to one embodiment, an implantable strain sensor is described. A strain sensor can include an indicator that includes a first end that is configured for fixation to an orthopedic implant (e.g., integral to, directly or indirectly bonded or otherwise attached to, etc.). For instance, a first end can be affixed in a sensor housing that is attached to an orthopedic implant such as a fixation device, a joint replacement component, a dynamic hip screw, etc. The indicator can also include a second end. During use, the second end can exhibit motion relative to the implant in response to a load placed on the implant either directly or indirectly.

According to another embodiment disclosed is an implantable chemical sensor that includes an indicator. In this embodiment, the indicator can include an analyte-sensitive material and a radiographically discernable component that is configured to exhibit motion in response to an analyte interaction with the analyte-sensitive material that leads to a dimensional change in the analyte-sensitive material.

In addition, a sensor (a chemical sensor or a strain sensor) can include a scale that is located in proximity to the discernable structure such that the location of this structure (e.g., the end of an indicator rod) with respect to the scale is radiographically discernible, e.g., the end of the indicator can overlay the scale in a radiographic image.

Also described are orthopedic implants such as fixation plates, screws, rods, or pins, and the like directly or indirectly held in conjunction with a sensor.

Methods for determining health of tissue by use of the sensors are also described. For instance, a method can include placing orthopedic tissue (e.g., a bone) under load. The tissue can have affixed thereto an orthopedic fixation component (e.g., a fixation plate, rod, screw, etc.) that carries a sensor. A method can also include examining the sensor via a radiographic imaging process while the tissue is under the load. Through examination of the sensor, the location of the second end of the indicator in relation to the scale can be discerned.

In one embodiment, a method can determine chemical conditions in the local area of an implant. For instance, upon interaction with a predetermined analyte (e.g., a pathogen or a pathogen determinant), a radiographically discernable component of the sensor can move in relation to the tissue and/or the implant due to, e.g., the swelling of the indicator of the sensor.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 19 schematically illustrates at A a bone having a 1 cm osteotomy and affixed support plate including a sensor as described. At B is shown the sensor for the bone under no load and under a 400 N load. An intact bone with support plate affixed is shown at C, and at D is shown the sensor for the intact bone under no load and under a 400 N load.

FIG. 20 illustrates a femur including a titanium dynamic hip screw affixed thereto (left), and a femur including a stainless steel dynamic hip screw affixed thereto (right).

FIG. 30 illustrates at A a bone under increasing loads with a supporting plate and sensor affixed thereto. The relationship between the displacement of the load indicating rod and the maximum callus strain is graphically illustrated at B.

FIG. 31 graphically illustrates the response of sensor with variation in load (left), callus stiffness (center) and compression (right).

FIG. 32 illustrates a chemical sensor at two different pH levels.

FIG. 33 illustrates the repeatability of the response of the sensor of FIG. 32

FIG. 34 illustrates the fixation and response of a chemical sensor on a cadaver tibia including a fixation device.

Figure 1A:
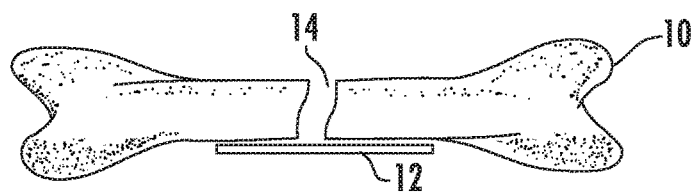
FIG. 1 schematically illustrates a broken bone affixed to a supporting device at A, the broken bone under a load at B, and the bone under a load after an amount of healing at C.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to devices and methods for determining bone health. More specifically, disclosed are sensors that can be utilized in conjunction with orthopedic implants that can provide information with regard to the ability of orthopedic tissue (e.g., bones, ligaments, tendons, etc.) to support a load and/or the presence of infection or other health issue in the area of an implant. Beneficially, the sensors are passive and can be read by use of standard radiographic imaging techniques (e.g., X-ray, computed tomography (CT) scanning, etc.) that are already taken as part of a standard patient evaluation. Moreover, the sensors can be affixed to known implantable support devices (e.g., tibial plates, spinal inserts, screws, rods, pins, etc.) without excessive modification of the implants so as to non-invasively monitor the implant to provide a quantitative assessment of one or more characteristics in the local area of the implant.

In one embodiment, the passive sensor can be a strain sensor that can be utilized to determine when a damaged bone, joint, or soft orthopedic tissue is sufficiently healed to allow safe weight-bearing upon the limb. While the bulk of this application discusses utilization of disclosed sensors in conjunction with bones, it should be understood that disclosed sensors can be utilized in conjunction with any orthopedic implant and any orthopedic tissue including, without limitation, bone, ligament, tendon, meniscus, etc. The strain sensors are based upon the transition of load from a supporting implant to the orthopedic tissue (e.g., bone) as the tissue heals and becomes stronger. For instance, at initial fixation, a fractured bone can take little or no load without possibility of further injury. As such, most or all of a load (e.g., an axial load in the case of a long bone) placed on the bone will be carried by the supporting orthopedic implant structure.

Figure 1B:
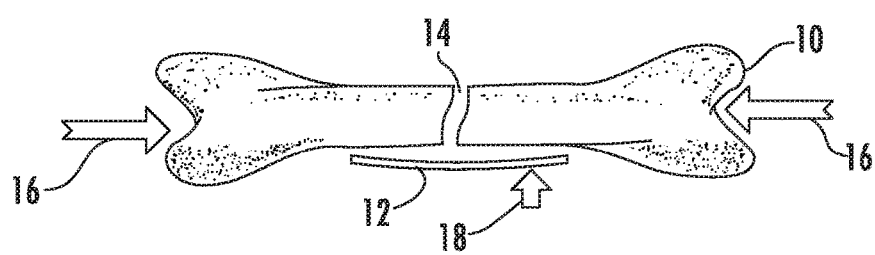
Figure 1C:
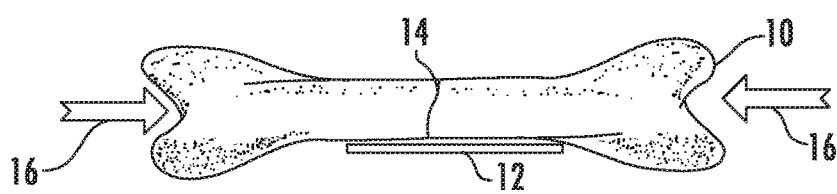

To illustrate, FIG. 1 at A schematically illustrates a fractured bone 10 with an orthopedic fixation device 12 affixed to the bone 10. As shown, the fixation device 12 spans the fracture 14 and supports the bone 10. As shown at B, the fixation device 12 is off of the axis of the bone 10. When an axial load 16 is placed on the bone, e.g., during standing or walking, the fractured bone 10 cannot support the load 16 and at least a portion of the load 16 will be translated to a load 18 on the fixation device 12 causing the fixation device 12 to bend. Though illustrated as a compressive axial load, disclosed strain sensors can indicate transference of a load from a bone to an attached orthopedic implant and/or direct load on an orthopedic implant for any load applied in any direction and any degree of freedom including any one or any combination of compression, extension, and torsion loads. Exemplary loads can include, without limitation, axial compressive loads, axial extension loads, transverse bending loads, transverse compressive loads, axial torsion loads, and/or compressive, extensive, or torsion loads applied at any angle to an axial direction of a bone or sensor.

As the bone 10 heals, it becomes strong enough to carry more and more of the load 16. For instance, as shown at C of FIG. 1, following a period of healing (for instance when the fractured bone has about 25% or more of the bending stiffness of intact bone), an axial load 16 placed upon the bone 10 can be carried by the bone 10 with little or none of the load translating to the fixation device 12. As such, the fixation device 12 will exhibit little or negligible bending. As is known, some degree of load placed on the bone can stimulate bone growth, and as the bone heals bending of the fixation device will decrease as the bone heals and shares more of the load. For instance, animal models that examined plate strain via percutaneous access showed decrease during walking as the bone healed.

The passive strain sensors have been designed around the concept of the load transference from an orthopedic fixation device to the surrounding tissue that takes place during normal healing. The sensors can be utilized to determine the distribution of a load between a bone and a fixation device and as such, can provide an indication of the bone health and level of healing. The passive sensors can be mounted to orthopedic devices so as to non-invasively serve to quantify implant bending/deflection using standard radiography. In some embodiments, the strain sensors can amplify the normal deflection of an orthopedic implant to provide clear indication of the load transfer to an implant. This can provide quantitative thresholds for safe weight bearing during rehabilitation so as to not only prevent complications due to load bearing too soon in the healing process but also to stimulate bone growth through increased load bearing as the healing process progresses. Through use of the sensors, a care giver can identify the point at which a fracture has sufficiently healed so that safe weight bearing and rehabilitation may begin as well as recognize when healing is insufficient for such weight bearing in order to reduce complications from premature weight bearing and for the early detection of possible complications such as fracture nonunion.

Beneficially, the sensors are passive, and as such require no internal energy source or active interrogation for examination. The sensors can be easily read with standard radiography available in all hospitals and many clinics and can be incorporated into existing implant constructs to provide robust, durable performance for use in conjunction with any orthopedic tissue. The sensors can be incorporated with fixation devices in a wide variety of orthopedic applications in addition to long bone fixation applications including, without limitation, spine fusion, hip fixation, total or partial joint replacement of any joint, and others to provide mechanical and mechanically transduced orthopedic measurements. Implantable orthopedic components of interest include, without limitation, cervical spine plates, spinal fusion devices, dynamic hip screws, compression plates, locking plates, screws, intramedullary rods, etc.

Figure 2:
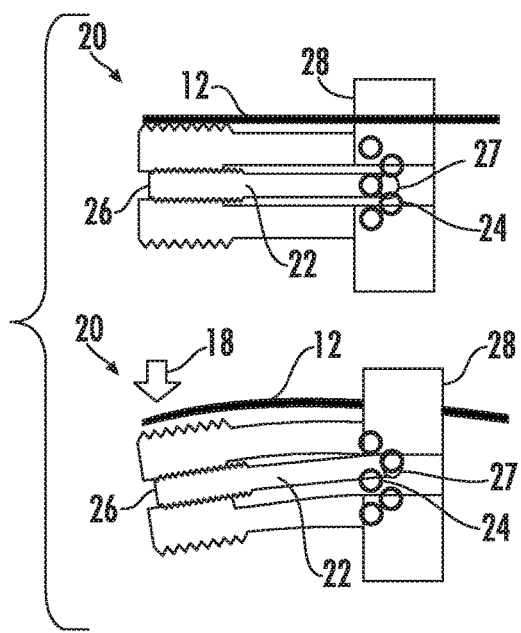
FIG. 2 illustrates one embodiment of a sensor as disclosed herein under no load (top panel) and under a load (bottom panel).

One embodiment of a strain sensor 20 is illustrated in FIG. 2. A sensor 20 can include an indicator 22 and an internal scale 24. The internal scale 24 can be used to quantify bending of a fixation device as an accurate and reproducible characterization of fracture healing via radiographs. The indicator 22 of a strain sensor can be a load indicator and can include a first end 26 and a second end 27. A first end 26 of the indicator 22 can be configured so as to be directly or indirectly joined to an implantable orthopedic fixation device. For instance, in the embodiment illustrated in FIG. 2, the first end 26 of the indicator 22 is held by a housing 28 that can be attached to an orthopedic fixation device, e.g., a fixation plate 12. The first end 26 of the indicator 22 can be directly attached to the orthopedic device or to a housing that is in turn attached to an orthopedic device. In any case, the first end can be attached such that there is little or no relative motion between the orthopedic implant and the first end 26 of the indicator 22 when the bone is placed under a load, even in those cases in which the full load is transferred from the bone to the orthopedic implant. Attachment mechanisms can be any suitable mechanisms as is known in the art, including as a monolithic component of the device as formed or via attachment following formation. Attachment mechanisms can include utilization of adhesives, screws, pins, melt bonding, etc.

In one embodiment, the first end 26 of the indicator 22 can be fixed to a portion of the fixation plate 12 that is expected to exhibit a large movement distance when the bone to which it is attached is placed under load. For instance, when considering a long bone fixation plate 12, the sensor 20 can be located on the fixation plate 12 such that the first end 26 of the indicator 22 is near or at the end of the fixation plate 12. As such, when the bone to which the plate 12 is attached is placed under a load (as illustrated in FIG. 1), and when a portion of that load 18 is transferred to the fixation plate 12 causing the plate 12 to bend (FIG. 2, bottom panel), the first end 26 of the indicator 22 can be at or near the locale of maximum movement distance.

The second end 27 of the indicator 22 is free to move relative to the fixation plate 12 and the bone to which the sensor is attached. For instance, if the sensor 20 includes a housing 28, the second end 27 can be located such that it is not fixed to the housing 28.

A housing 28 can be of any suitable design and material so as to protect the sensor and not interfere with sensor function and radiographic imaging. For instance, a housing can be made of rigid or semi-rigid biocompatible and implantable formation materials, and at least that portion of a housing 28 that covers a scale 24 can be radiographically transparent. In one embodiment, a non-immunogenic, radiographically transparent material can surround at least the second end 27 of the indicator 22 to allow the second end 27 to move relative to the fixation plate 12 while also forming a barrier between the second end 27 and surrounding tissue and allowing the second end 27 to be observed via radiographic imaging.

The lower panel at FIG. 2 demonstrates the reaction of the sensor 20 under a load 18. As shown, the housing 28 and the first end 26 will move with the fixation plate 12 as it bends under the load 18. However, the second end 27 is free to move with respect to the fixation plate 12 and will not bend with the fixation plate 12. Thus, there will be a relative motion between the fixation plate 12 and the second end 27. The internal scale 24 is also fixed to the housing 28 and/or the fixation plate 12 and is located such that the relative motion between the fixation plate 12 and the second end 27 can be discerned on the internal scale 24.

In the embodiment of FIG. 2, the indicator 22 is in the form of an elongated pin or rod having an aspect ratio (length divided by width) of greater than 1. At least the second end 27 of the indicator 22 can be formed of a radio-opaque material such as, e.g., tungsten, so as to be clearly visible during use.

The direction of movement of the indicator of the sensor is not particularly limited. For instance, with the lever-type indicator of FIG. 2, the direction of motion of the second end 27 of the sensor 20 can be generally parallel to the direction of the load 18. This is not a requirement, however, and in other embodiments, the second end of the load indictor can move in other directions. For example, the sensor 120 illustrated in FIG. 3 includes a housing 128, a scale 124, and an indicator 122, the second end of which 127 moves in a direction generally normal to the direction of the load 18. As illustrated, the load indicator 122 includes a first end 126 that is configured to be held directly or indirectly to the fixation plate 12 (e.g., via the housing 128). Upon placement of a load 18 on the sensor 120 the first end 126 is compressed. The compression of the first end 126 causes the second end 127 to elongate and thereby to move in a direction generally parallel to the axial direction of the indicator 122 and normal to the direction of the load 18.

The capability of elongation of the second end 127 can be provided by formation materials of the indicator 122. For instance, the indicator 122 can include an extendable and radiographically visible material, e.g., an elastomeric solid, a gel, or a liquid that can extend at the second end 127 upon compression of the first end 126 such that the extension is radiographically discernible. The fluid or gel can serve as a transducer to convert motion in one direction to motion in another direction, as is well known in hydraulic and pneumatic actuation systems, optionally with amplification. A radio-opaque fluid may be used, (e.g., a solution with a high concentration of a high atomic element, such as mercury; gallium; galistan; water solutions with rare earth nitrates; and dispersions of radio-opaque micro- or nanoparticles such as, but not limited to, gold nanoparticles, tungsten nanoparticles, bismuth nanoparticles, and gadolinium oxysulfide microphosphors. In addition to a radio-opaque fluid or gel, a radiolucent fluid may be used to push a radio-opaque marker such as, but not limited to, a tungsten pin or tantalum bead. Elastomers including, but not limited to, polydimethyl siloxane (PDMS), acrylic elastomers, and others can also be used in place of a hydraulic or pneumatic system: When load is applied in one direction due to applied load, elastomers generally expand in other directions, a phenomenon known as the Poisson effect. For example, when a spherical PDMS gel containing radio-opaque gadolinium oxysulfide microphosphors is pressed between two flat surfaces, it becomes roughly disc shaped with a diameter that increases with increasing load, and this change in diameter of a sensor indicator can be observed using radiography.

Figure 3:
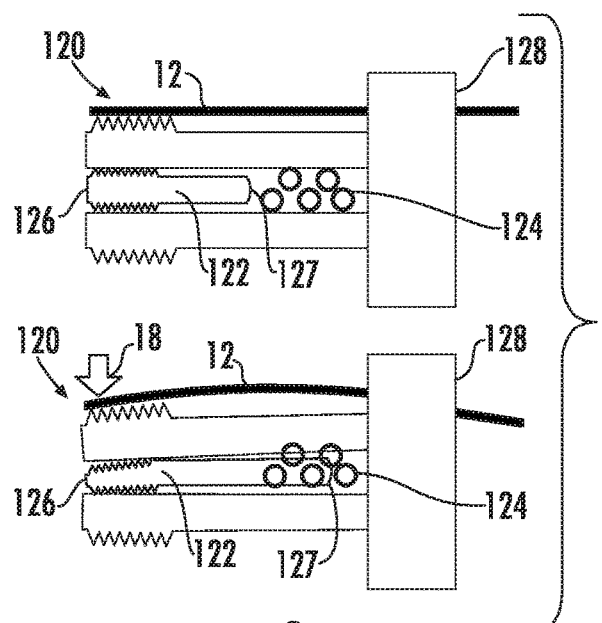
FIG. 3 illustrates another embodiment of a sensor as disclosed herein under no load (top panel) and under a load (bottom panel).

As illustrated in FIG. 2 and FIG. 3, a sensor can include an internal scale 24, 124 that can be used to indicate relative motion between the second end 27, 127 of the indicator and the fixation plate 12. The scale of a sensor can be located and arranged so as to clearly discern the position of the second end of an indicator with respect to the fixation device to which the sensor is attached. For example, in the embodiments of FIG. 2 and FIG. 3, the scales 24, 124 are rotated with respect to one another so as to more clearly discern the position of the second end 27, 127 of the indicators 22, 122, respectively. This rotation is indicated in order to fully encompass the direction motion of the indicators 22 (i.e., lever-type indicator) and 122 (extendible-type indicator).

Figure 4:
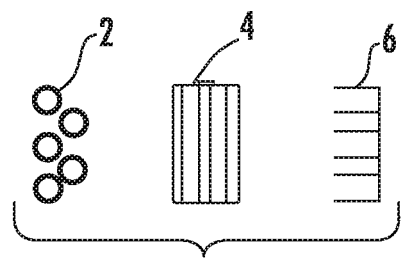
FIG. 4 illustrates representative examples of scale designations as may be utilized with a sensor.

In the embodiments of FIG. 2 and FIG. 3, the internal scale 24, 124 is provided as a series of round markings in/on the housing 28,128. For instance, the markings can be formed of a material that is radiographically discernable from the surrounding material of the housing. By way of example, a scale 124 can include a series of markings (e.g., circles) formed of a radio-opaque material such as tungsten that are surrounded by a radiographically transparent material. It should be understood, however, that the form of the internal scale is not critical, and any scale form, shape, or material that is radiographically discernible from the surrounding material is encompassed herein. For instance, FIG. 4 illustrates several different scale configurations including circular apertures 2, trenches 4, linear markings 6, etc. Any scale that can demonstrate relative motion between a movable segment of a sensor indicator and the orthopedic fixation device to which the sensor is affixed is encompassed herein. In addition, in one embodiment a scale 124 can include predetermined markings (e.g., circles, bars, lines, etc.) that are set at a physiologically relevant threshold so as to determine safe or unsafe weight bearing when the affixed bone is placed under a load.

The dimensions of the indicator and/or the scale can be suitable so as to provide a radiographically determinable indication of movement of the attached orthopedic device. For instance, a relatively long lever-type indicator such as that of FIG. 2 can amplify the movement distance of the orthopedic device so as to more accurately determine the distance of motion of the orthopedic device and more accurately determine the load on the orthopedic device. In one embodiment, the indicator may be tapered to provide both a relatively thick rigid base and a finer tip for pointing at the scale.

Figure 5:
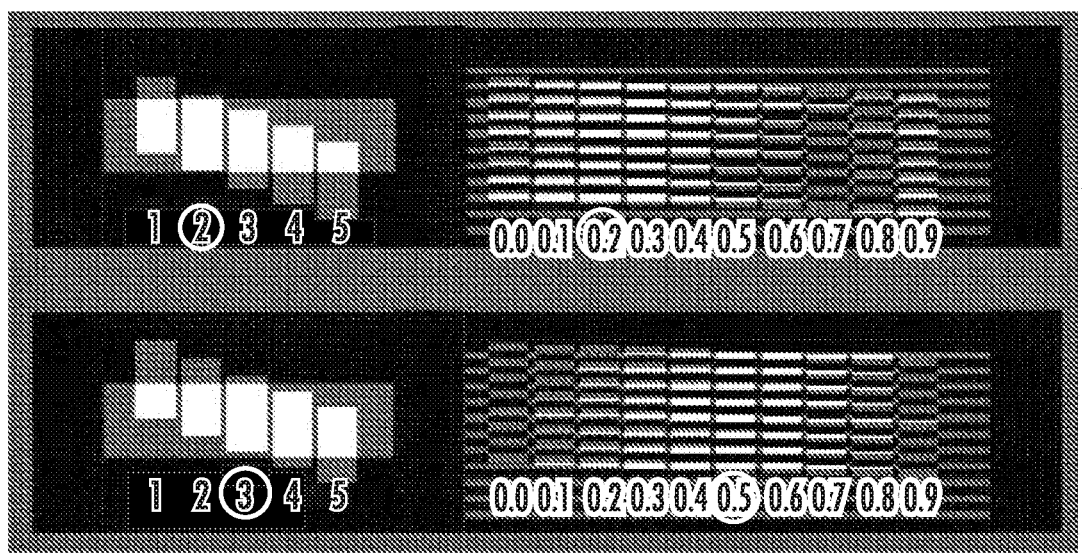
FIG. 5 illustrates a Vernier-type scale for a sensor as disclosed herein that incorporates moiré fringes.

In some embodiments, the scale may have finely designed features (e.g. holes) to allow visualization of small motions, for instance by use of a Vernier-type scale based upon moiré fringes as illustrated in FIG. 5. Other amplification techniques, based upon gears, levers, pulleys, hydraulics, pneumatics, etc. can be used. For instance an extendable-type indicator can incorporate a relatively small cross sectional area for the extendable material, and a relatively small motion of an attached orthopedic device can be amplified to a relatively long extension of the indicator. By way of example, when considering a hydraulic system using an essentially incompressible fluid, in order to conserve fluid volume, the displacement of the fluid within a tube is generally the ratio between the area of the piston or region pressing on the fluid to the area of the fluid in the tube (e.g. if a 10 mm$^2$ area piston moves 200 μm as it pushes fluid through a 1 mm$^2$ tube, the fluid in the tube would move 2 mm). The same principle also applies to fluids being pushed by a bulb instead of a piston.

Figure 6:
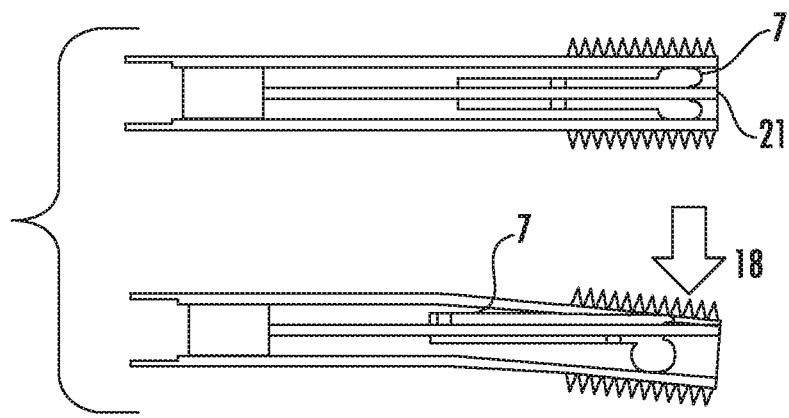
FIG. 6 illustrates a sensor in which the sensor incorporates a hydraulic amplification system.
Figure 7:
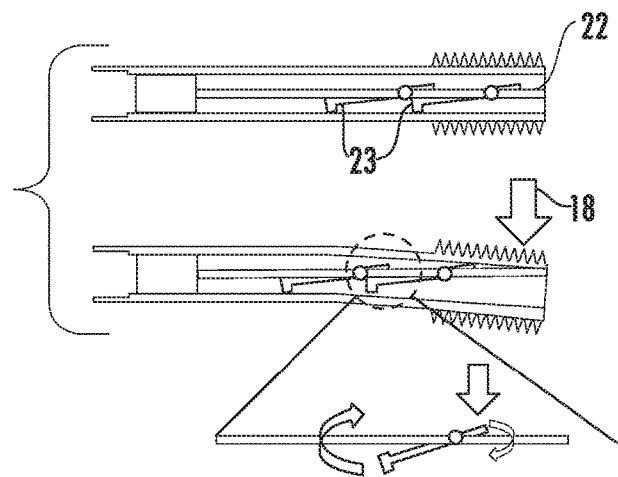
FIG. 7 illustrates a sensor in which the sensor incorporates a lever-based amplification system
Figure 8:
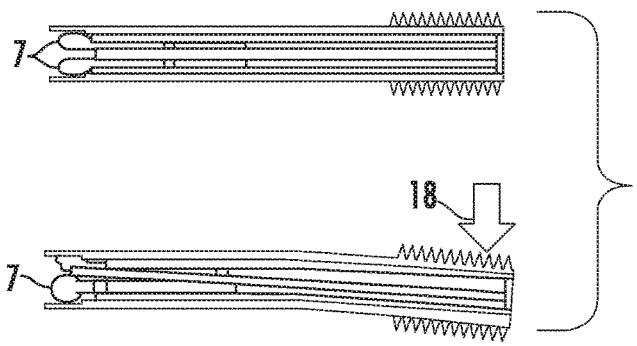
FIG. 8 illustrates a sensor in which the sensor incorporates a hydraulic amplification system.

Amplification of the distance of motion of an orthopedic device at the sensor indicator can improve accuracy of the devices. By way of example, FIG. 6, FIG. 7 and FIG. 8 illustrate exemplary amplification systems. In the system of FIG. 6, the system can include an extendable material 7 that can be a component of an indicator that also includes a lever arm 21 as described above. Upon relative motion between the lever arm 21 of the indicator and an orthopedic device (not shown in FIG. 6) due to a force 18, the extendable material 7 can be extended, and the change in location of an end of the indicator (e.g., the end of the extendable material 7) can be radiographically discernable. FIG. 7 illustrates another embodiment in which the indicator 22 includes a series of lever arms 23 the response of which to a force 18 on the sensor can amplify the distance that is moved by the orthopedic implant (not included in FIG. 7). In the embodiment of FIG. 8, a sensor including an extendable material 7 is illustrated. In this embodiment, when the sensor is placed under a load 18, the extendable material 7 retracts. Any combination of materials and geometries as are known in the art can be utilized to amplify a radiographically detectable signal of a sensor. Of course, amplification of a signal is not a requirement of a sensor. In general, the ratio of distance of motion of an orthopedic implant to distance of motion of a second end of an indicator can be from about 1:1 to about 1:100, from about 1:2 to about 1:50, or from about 1:3 to about 1:10 in some embodiments. In some embodiments, a fine and course scale can be used. Of course, the size of the sensor components will also depend upon the size and shape of the particular fixation device used with the sensor.

Figure 9:
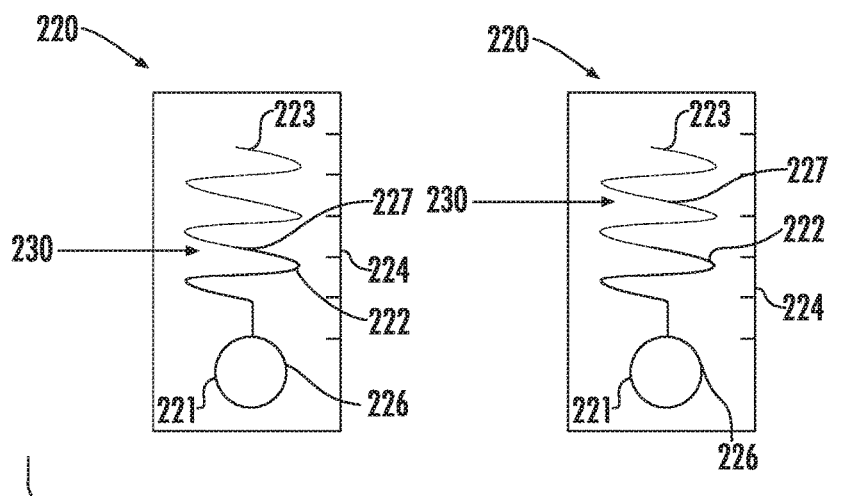
FIG. 9 illustrates another embodiment of a sensor has disclosed herein under no or low load (left panel) and under a greater load (right panel).

FIG. 9 illustrates another example of a sensor 220 that includes an indicator 222 formed of an extendable material. In this embodiment, the indicator 222 can be a radiographically discernible liquid, solid, or gel as discussed above confined to a reservoir 221 at a first end 226 of the indicator 222 and a track 223 along which the extendable material can travel. During use, the sensor 220 can be located in conjunction with an implantable orthopedic device such that upon motion of the orthopedic device (e.g., bending as shown in FIG. 1 at B), a portion of the orthopedic device contacts the reservoir 221 at the first end 226 and forces the indicator 222 along the track 223. The distance moved by the second end 227 of the indicator 222 (as indicated by the arrows 230 on the left and right panels of FIG. 5) can be radiographically discernible. A scale 224 can be included on a sensor 220 as a series of markings, as shown. Alternatively, another component of the sensor 220 can be utilized as the scale. For instance, the turnings of the track 223 can be used as an internal sensor scale to indicate the distance moved by the second end 227 of the indicator 222, and this movement distance can be correlated to a load on the orthopedic implant to which the sensor is attached.

Figure 10:
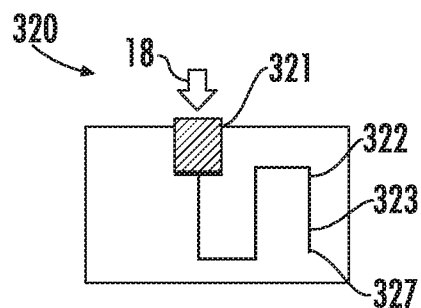
FIG. 10 illustrates another embodiment of a sensor.
Figure 11:
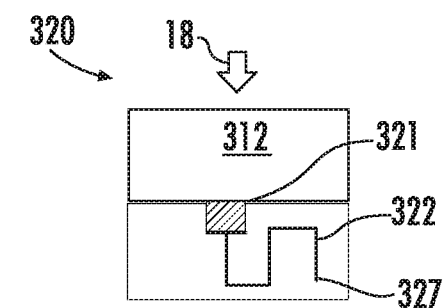
FIG. 11 illustrates another embodiment of a sensor.

FIG. 10 illustrates another embodiment of a sensor 320 that includes an extendable indicator 322. In this embodiment the sensor 320 can include a piston 321 that can transfer a load 18 to an extendable indicator 322 held in a track 323. For instance, as illustrated in FIG. 11, a sensor 320 can be located adjacent to an implantable orthopedic device 312 and a load 18 transferred to the device 312 from a bone to which the device 312 is attached can be determined through examination of the sensor 320, and in particular, through determination of the distance of motion of the second end 327 of the indicator 322 when the device 312 is under the load 18.

As discussed above, an orthopedic implant for use with disclosed sensors is not limited to a fixation plate for a long bone. In one embodiment, a strain sensor can be utilized in conjunction with a spinal surgical instrumentation system, including those of spinal fusion operations and arthroplasty (artificial disc) operations. Such systems may include, by non-limiting example, anterior cervical discectomy and fusion (ACDF) systems, Anterior Lumbar interbody systems (ALIF), posterior instrumentation, artificial disc placement systems, and laterally placed anterior lumbar interbody spacers.

Figure 12:
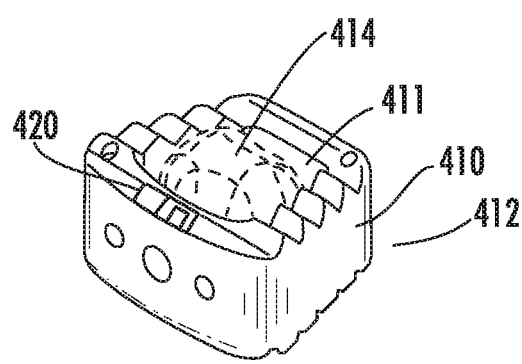
FIG. 12 illustrates an anterior spinal interbody device (ACDF or ALIF) spine insert including a sensor.
Figure 13:
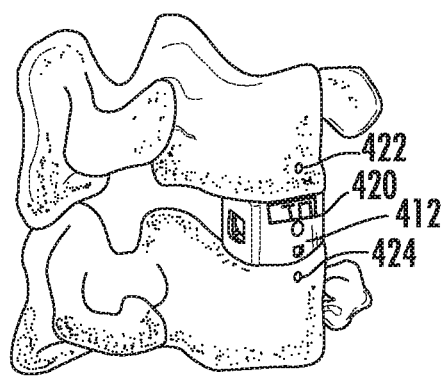
FIG. 13 illustrates an anterior spinal interbody device (ACDF or ALIF) spine sensor including a sensor following implant.

FIG. 12 illustrates a fusion assembly 412 for use in an anterior spinal fusion (lumbar or cervical) that can be utilized in conjunction with a strain sensor 420. An assembly 412 can include a cage 410, and a bone graft 414 held within a lumen 411. During use, a surgeon determines the proper size cage 410 to fill the intervertebral space (FIG. 13). The surgeon then shapes the bone graft 414, typically an allograft (or autograft), to fit the lumen 410 of the cage 410.

An anterior interbody (lumbar or cervical) fusion operation includes surgical exposure of two or more cervical vertebrae (e.g., vertebrae 422, 424 of FIG. 13), removal of the disc between the two (discectomy and decompression), placement of an interbody assembly 412 between the vertebrae 422, 424 to maintain a desired spacing between the vertebrae allowing fusion of the two bodies by bone graft incorporation of the bone graft 414. Screw and plate stabilization is often added to improve fusion rates.

By use of a sensor 420 implanted in conjunction with the assembly 412, a caregiver can follow rehabilitation and fusion of the bone graft 414 with the adjacent vertebrae 422, 424. Prior to fusion of the bone graft 414, a load placed on the assembly 412 can cause extension or compression of the distance between the vertebrae 422, 424, and this variation can be translated as an increase or decrease of strain on the assembly 412. By examining the sensor 420, and determining the location of the second end of the indicator (e.g., as illustrated in FIG. 10 and FIG. 11) when the assembly 412 is placed under a load, a caregiver can be informed as to the level of fusion of the bone graft 414. Specifically, early on in the healing process, when there is little or no fusion of the bone graft, the sensor can indicate a large response to an applied load. As the surgical site heals and the bone graft 414 fuses, the load will be increasingly taken by the implant and the fused graft, and the sensor 420 will exhibit a smaller response.

Figures 14A, 14B, 14C:
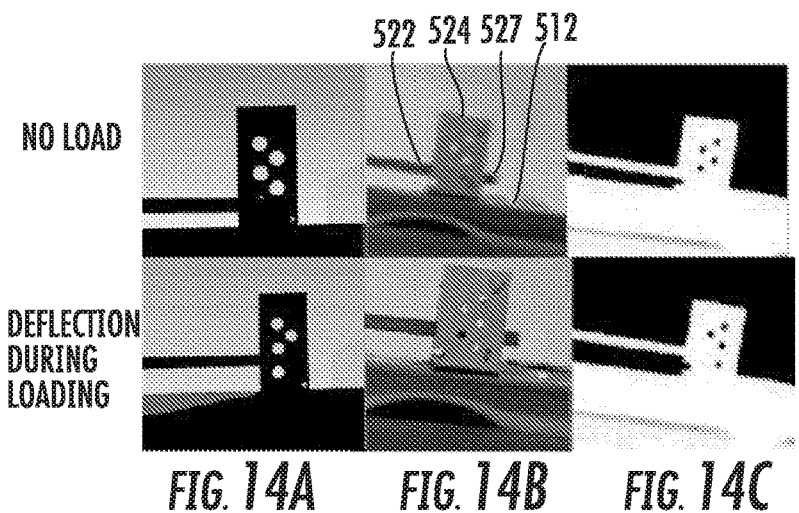
FIG. 14 illustrates the movement of a load indicator rod comparing the load indicator rod location on a sensor under no load (top panels) and under a load (bottom panels). Images include a finite element analysis (FEA) simulation at A, a photograph on a sawbone tibia model at B, and a radiograph on a sawbone tibia model at C.

FIG. 14 illustrates a portion of a lever-type sensor in which the scale 524 includes a series of radiographically discernible circular markings. Upon attachment to a fixation device 512, the second end 527 of the load indicator 522 is located in conjunction with the scale 524 such that the location of the second end 527 with respect to the scale 524 is discernable. In particular, when under a load if the second end 527 moves relative to the fixation device 512 (i.e., the fixation device bends or flexes), the change in position of the second end 527 from the zero point can be discerned by observation of the scale 524.

FIG. 14 includes views obtained from different imaging techniques of the second end 527 and scale 524 of a sensor lever-type indicator 522 under no load (top panels) and under a load (bottom panels) causing deflection of the fixation device 512 that is attached to both the sensor and a sawbone tibia model. The imaging techniques include an FEA simulation at A, a photograph at B, and a radiograph at C. As can be seen, under no load, the second end 527 of the indicator 522 is aligned with the bottom-most opening of the scale 524 (i.e., a predetermined zero point). When the tibia is placed under a load, the second end 527 moves relative to the scale 524 and the second end 527 is now aligned with the second of the five openings of the scale 524. Thus, it can be determined that at least a portion of the load on the tibia has transferred to the fixation device 512.

Figure 15:
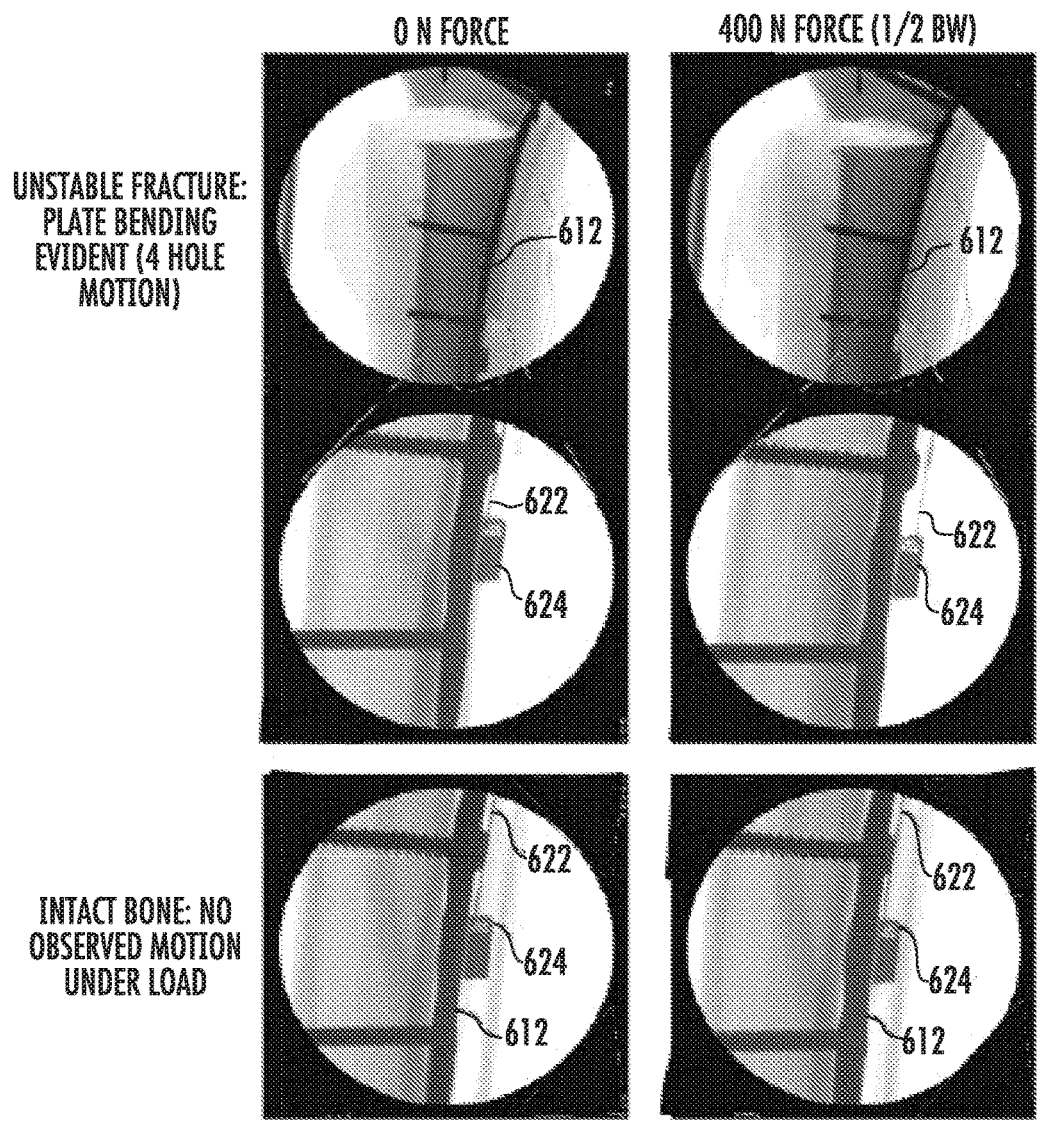
FIG. 15 presents radiographic images of a human tibia cadaver model under no load (left column) and under a 400 Newton (N) load (right column). Images include those of a plated fractured tibia (top panels) and a plated intact tibia (lower panels).

A sensor can be attached to an orthopedic implant by any means and at any convenient location provided that the scale can be read radiographically and the sensor does not interfere with bone healing. FIG. 15 illustrates one exemplary mounting of a sensor on a long bone fixation device 612. As shown, the sensor is mounted such that the lever-type load indicator 622 is attached to the surface of a plate fixation device 612. Using radiography, the position of the second end 627 of the indicator 622 can be seen with respect to the scale 624 and the movement due to the load transference to the implant 612 can be observed. As shown, the scale 624 indicates no relative motion between the second end 627 of the load indicator 622 and the scale 624 when an intact human cadaver tibia is loaded with a 400 N force (bottom panels). In contrast when examining a load on an unstable fracture (upper panels), significant relative motion of the second end 627 of the load indicator 622 can be seen by examination of the scale 624 between a no-axial load position and a 400 N axial load on the bone (½ body weight load).

There is no particular arrangement of components or mounting orientation required for a sensor. For instance, in the embodiments of FIGS. 14 and 15, the indicator second end is observable behind the scale. However, a scale of a sensor can be formed so as to be visible from any one or multiple views of the indicator or off-set to a greater or lesser degree. For instance, the scale can be a part of a track filled by the indicator as discussed above. Alternatively, a portion of an implant can be used as the scale (e.g., the threads on a screw, bolt, hole, etc.) or markings on an implant component. For instance, a scale can be located within or formed along the edge of an aperture of the orthopedic implant (e.g. within an unused screw hole). In such embodiment, the second end of the indicator can pass above the scale, and the scale can be read by an overhead view of the aperture.

In any case, the sensor components can be located such that they do not interfere with proper function of the implant and such that they do not cause irritation at the implant site. For instance, a sensor can be located at one side of a compression plate and optionally can utilize unused screw holes. In general, a sensor can have a relatively small profile and can either be set within the profile of the associated orthopedic implant or can extend to a small degree beyond the surface of the orthopedic implant. This can be particularly beneficial when considering a sensor for use in conjunction with an implant configured for location deep within tissue.

Figure 16:
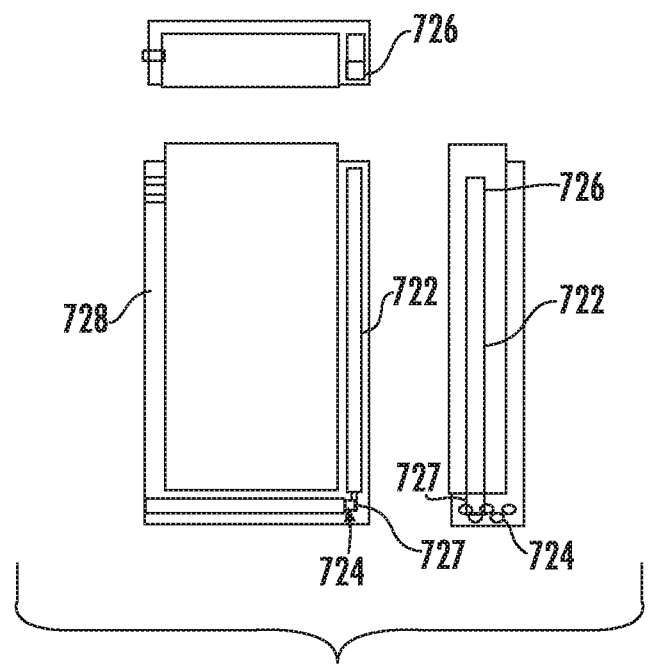
FIG. 16 schematically illustrates a top, front, and side view of a sensor.

One embodiment of a low-profile sensor is illustrated in FIG. 16. As shown, the sensor can include a radio-opaque indicator 722 that includes a first end 726 and a second end 727. The second end 727 being arranged such that its location is discernable with respect to a scale 724 that includes a series of markings formed as apertures in a radio-opaque material. Accordingly, relative motion between the second end 727 and the scale 724 can be observed when a load is sufficient to cause bending of the attached implant.

The sizes and materials of the various components of a sensor can vary depending upon the particular design of the sensor and the orthopedic implant to which the sensor will be attached. For instance, the cross sectional dimension of the scale features (e.g., the diameter of the circular markings of the scale 724 of FIG. 16) can generally be from about 0.05 mm to about 1 mm, such as about 0.5 mm in some embodiments, and can be spaced apart from one another at a similar distance (e.g., from about 0.5 mm to about 1 mm) so as to be clearly discernible during imaging. Smaller increments can generally be detected using higher resolution/magnification X-ray imaging setups and/or moiré patterns and/or image analysis algorithms. The second end 727 of the load indicator can likewise be sized so as to be clearly discernible when viewed against the scale 724. For instance, a second end 727 of an indicator 722 can have a width of from about 0.5 mm to about 1 mm. As discussed above, the location and dimensions of an indicator can be designed to amplify the motion distance of the orthopedic implant and more clearly discern the load transferred to the orthopedic implant. As such, a lever-type indicator (or track of an extendible indicator) can be quite long, e.g., from about 2 cm to about 20 cm in some embodiments, or even longer in some embodiments.

The materials utilized to form a sensor can be chosen in order to clearly discern the relative motion of the second end of the indicator against the scale. For instance, at least the second end of the indicator and the scale markings (e.g., the circles) can be formed of a radiographically discernible material, e.g., tungsten, tantalum, stainless steel, etc.

When included, a housing 728 of a sensor can be radiographically transparent or opaque, depending upon the nature of the indicator and scale materials, the arrangement of the various sensor components, the implant type to which the sensor is to be fixed, and so on, as would be evident to one of skill in the art.

Figure 17:
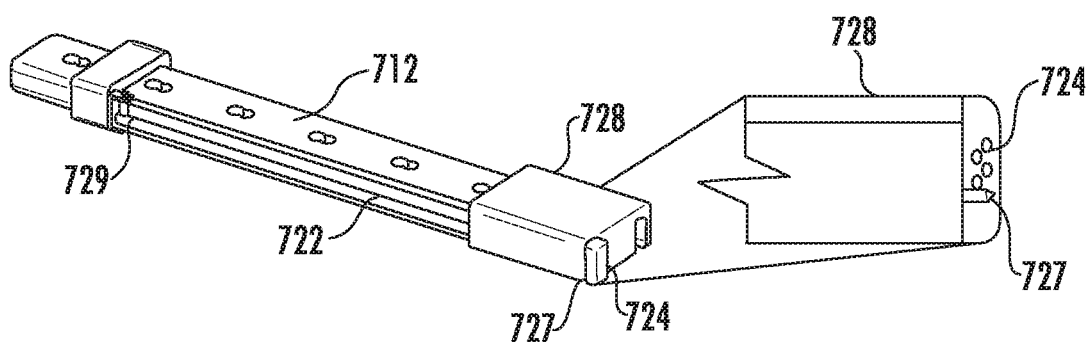
FIG. 17 schematically illustrates a sensor as illustrated in FIG. 16 affixed to an orthopedic fixation plate.

FIG. 17 illustrates the sensor of FIG. 16 attached to a bone fixation plate 712. As shown, the sensor is attached so as to present a relatively low profile against the plate 712 while still being capable of being read by imaging the plate 712 from the proper orientation. Generally, the second end 727 and the scale 724 can be protected from the environment of the surrounding implant area, for instance by use of a radio-lucent formation material. By way of example, all or part of a sensor can be surrounded by a radio-lucent polymeric material.

A sensor can include a calibration/adjustment mechanism to properly align and zero the indicator and scale upon implant. For instance, and with reference to FIG. 17, a sensor can include an adjustment set screw 729 (or equivalent) that can be used to adjust the initial zero position of the second end 727 of an indicator 722 in relation to the scale 724 upon attachment of the orthopedic implant to adjacent bones when under no excessive load. For example, the second end 727 of the indicator 722 may be adjusted and/or the scale 724 can be moved to zero the sensor at initial implant of the orthopedic device. Of course, a zeroing adjustment can be carried by any useful means and mechanisms.

A sensor can be formed as a unitary part of an orthopedic fixation device at manufacture or can be mounted to a pre-existing orthopedic fixation device. For instance, a sensor can be added on to a fixation device following formation via any suitable attachment means. By way of example, the embodiment of FIG. 17 can be attached to an existing fixation plate by sizing the housing 728 to fit on the implant 712. Following proper location on the implant 712, the housing 728 can be locked into place by use of, e.g., a C-clamp, plate-on-plate attachment with screws into threaded screw holes in a locking plate, or attachment in a recess below the screw holes of the fixation plate 712.

Figure 18:
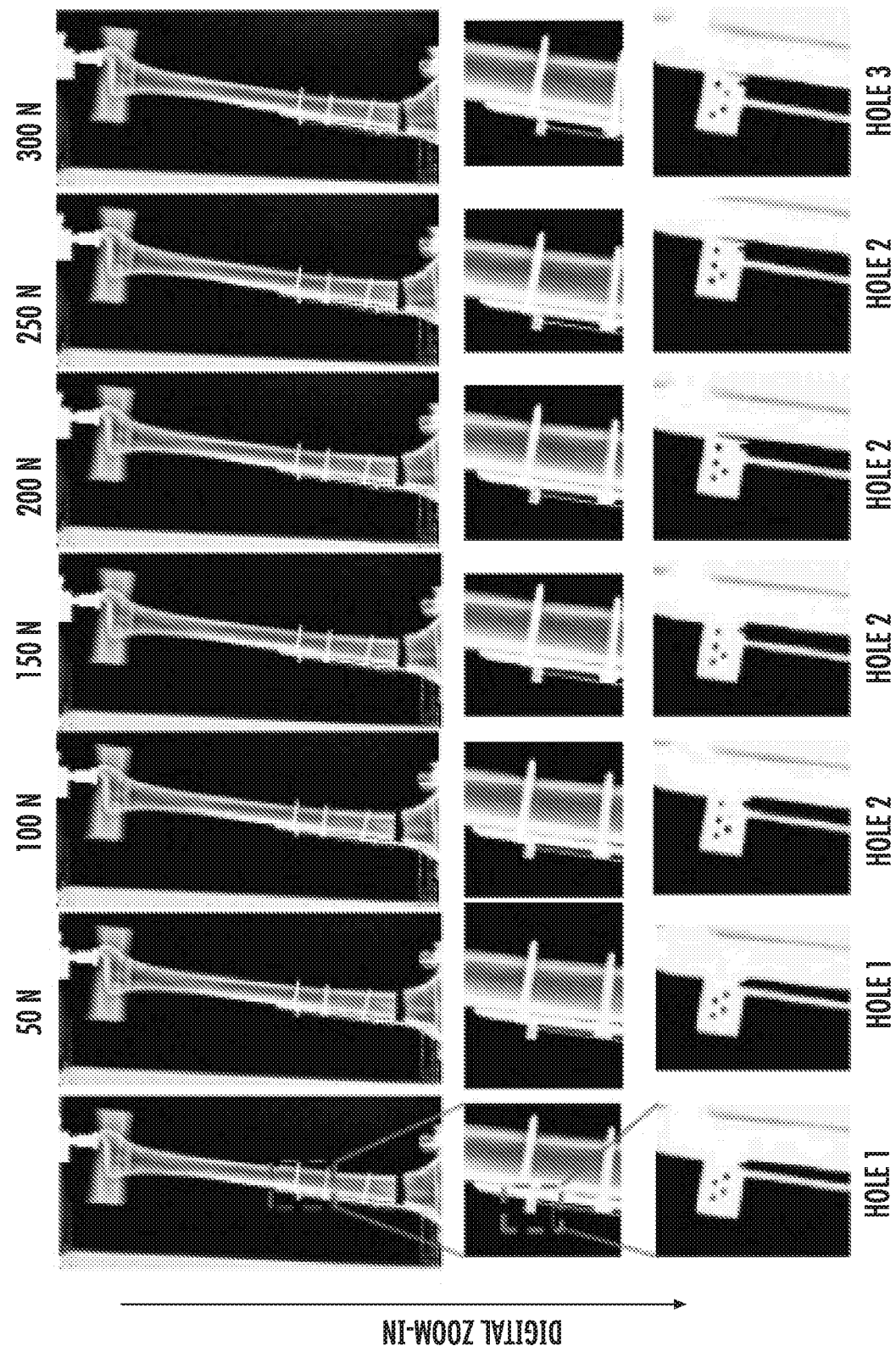
FIG. 18 illustrates radiographs of a plated fractured tibia under increasing load. The magnified images show the load indicator rod and the internal scale of the sensor.

FIG. 18 illustrates increasingly magnified views of a sensor utilized in conjunction with a broken tibia model. As shown, as the axial load on the tibia increases from 0 N to 300 N, the amount of load transferred to the attached fixation plate will likewise increase as the broken tibia is unable to carry little if any of the axial load. The load transferred to the attached fixation plate will manifest itself by causing the fixation plate to bend. The second end of the load indicator can be clearly seen in conjunction with the scale in the bottom-most panels. As shown, as the load increases, the location of the second end of the load indicator moves across the scale from the right-most hole in the first panel (Hole 1) to the center hole in the last panel (Hole 3).

An FEA simulation of strain and pin displacement for a fixation plate with a radiographic indicator is shown in FIG. 19. The strain on the construct with a 1 cm osteotomy (commonly used as an experimental model for unstable/comminuted fractures) under 400 N of axial compression load (at about ½ body weight) is shown in FIG. 19 at A. Due to the osteotomy, the load will be concentrated on the plate, and the sensor can detect plate bending by a change in the position of the second end relative to the scale. FIG. 19 at B shows the position of the second end under 0 and 400 N loads.

The simulation was repeated with an intact plated bone (representing bone before fracture or after complete healing). FIG. 19 at C shows the fixation device and sensor attached to the bone. FIG. 19 at D illustrates minimal strain on the plate from load sharing with the bone, as even under a 400 N load there is little or no displacement of the second end of the load indicator. Although a mid-shaft osteotomy is shown in FIG. 19, the same underlying mechanical principles can apply to proximal fractures as well as other orthopedic applications.

Of the two million fracture fixation surgeries each year in the U.S. 330,000 are for hip fractures. If the bone does not heal rapidly enough, the screws and other hardware can fail, which usually requires costly revision surgery and significant risk of morbidity and mortality. The most common hardware failure (75%) is from screw cutout with other significant failures from plate pullout, infection, and screw bending.

In one embodiment, disclosed sensors can be incorporated internal to an orthopedic implant rather than external as illustrated above. This may be a particularly beneficial approach in certain orthopedic applications such as joint replacements and hip implants, e.g., in repair of an intertrochanteric hip fracture, for measurement of load and excessive motion of one or more components of the implant.

In one such embodiment, a sensor can be incorporated within a dynamic hip screw. In this embodiment, the sensor can be utilized to radiographically indicate biomechanical bending of the screw in order to determine the extent of load sharing between the joint and the dynamic hip screw so as to determine whether the fracture is healed enough for weight bearing.

FIG. 20 illustrates a femur including a titanium dynamic hip screw (left) and a femur including a stainless steel dynamic hip screw (right) as examples of dynamic hip screws that can be implanted in conjunction with a sensor as described herein. In this embodiment, in which the orthopedic implant is designed for placement within bone tissue, it can be beneficial to incorporate the sensor within the implant, for instance within the cannula of a dynamic hip screw.

Figure 21:
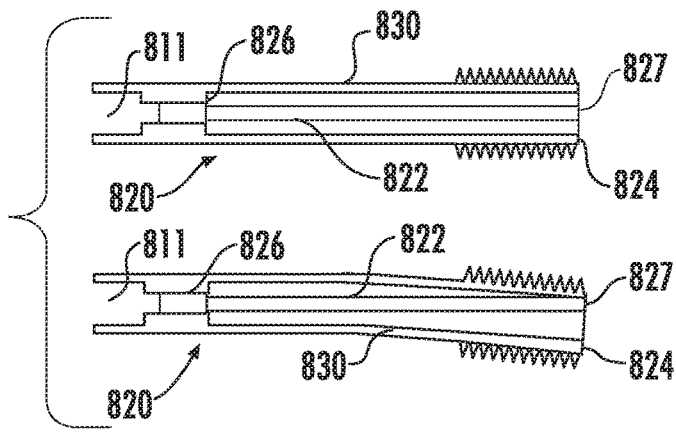
FIG. 21 illustrates a sensor as may be incorporated in a cannula of an implant (e.g., a dynamic hip screw).
Figure 22A:
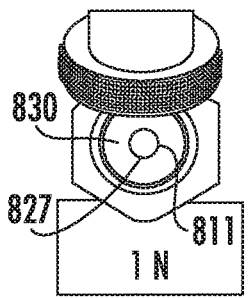
FIG. 22 illustrates end views of a dynamic hip screw including a sensor as illustrated in FIG. 21 (left panels) and a graph showing displacement of an indicator rod of the sensor under increasing load (right panel).
Figure 22B:
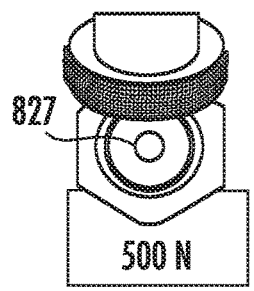
Figure 22C:
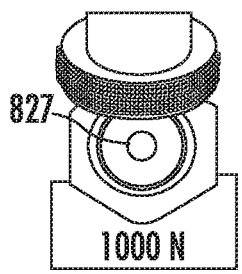
Figure 22D:
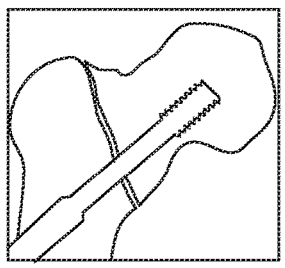
Figure 22E:
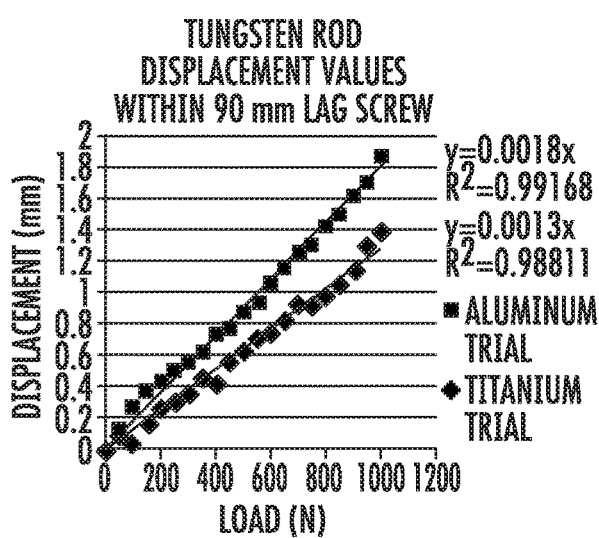

FIG. 21 illustrates a sensor 820 that can be incorporated within the cannula 811 of a dynamic hip screw 830. As shown, the sensor 820 includes an indicator 822 that includes a first end 826 and a second end 827. In this embodiment, the indicator 822 is a lever-type indicator. The scale 824 can be at the terminal portion of the hip screw 830 and under no load (top panel) the second end 827 of the indicator 822 is centered within the cannula 811. Under load (bottom panel), the second end 817 of the indicator 822 will move relative to the scale 824 (i.e., the outer ring of the hip screw 830), and the location of the second end 827 against the scale 824 can inform the caregiver that the dynamic hip screw is bending under the load applied to the hip.

FIG. 22 presents a side view of a dynamic hip screw implanted within a fractured femur and several end views of the dynamic hip screw 830 that includes a sensor within the cannula. Dynamic hip screws are designed to slide but not rotate, with physiological bending directed along one axis. As shown in FIG. 22, the second end 827 of the indicator can have some degree of play within the cannula 811 and will move relative to the hip screw when the screw is placed under load. The first end 826 of the indicator 822 can be fixed within the dynamic hip screw, for instance by threading, adhesive, melt bonding, etc.

By use of the disclosed sensors, bending of the dynamic hip screw can be observed directly by reference of the location of the second end 827 to a scale 824 that can be formed in the end of the hip screw or simply by utilizing the edge of the cannula 811 as the scale. In one embodiment, a scale 824 can be formed into or attached to the end of the dynamic hip screw to more clearly determine the load amount and direction. For instance, a scale can include markings on a cap (e.g., a radiolucent cap) that can be placed over the open end of the dynamic hip screw. This can not only provide a detailed scale but can also prevent bone in-growth into the cannula of the dynamic hip screw. Of course, a cap can be provided to cover an end of a dynamic hip screw that does not include scale markings thereon as well.

By observation of the scale 824 in an end view of the dynamic hip screw, the alignment of the second end 827 within the cannula 811 can be seen, and excessive bending of the screw 830 can be evident. For example, in the illustrated embodiment under a load of 1 Newton (N), the second end 827 is essentially centered within the cannula 811. As the load increases to 500 N, the second end 827 has moved off-center toward one edge of the cannula 811 and at a greater load of 1000 N, the second end 827 is pushed against the side of the cannula 811. The graph shown in the right panel of FIG. 22 presents the displacement distance of a cannulated tungsten rod with load for two trials. The rod was zero-centered within the cannula of a 90 mm lag screw for the trials.

Use of disclosed strain sensors can reduce complications from re-fracture or hardware failure by restricting weight bearing until a bone is sufficiently healed. The quantitative metric within the devices can identify patients with delayed and non-union fractures so that adjunctive therapies may be used. The sensors can also provide information such that normally-healing patients can begin weight bearing when a fracture sufficiently heals, generally earlier than current treatment protocols. These capabilities can result in reduced healthcare costs, earlier return to work, and improved quality of life.

In another embodiment, a sensor can be a chemical sensor that can be utilized to assess the local area of an implant for one or more analytes. For instance, an area can be assessed for the presence of an analyte that can indicate early stage infection at the implant site.

According to this embodiment, the indicator of a sensor can include a material that in the presence of a targeted analyte can exhibit a change that is detectable by radiographic imaging. For example, the indicator can exhibit a dimensional change upon interaction with the targeted analyte. The sensor can also include a scale as discussed above and optionally, a radiographically discernable component such as an extended rod, channel, or the like that can amplify and improve visualization of the dimensional change of the indicator in the presence of the analyte.

In general, an analyte-sensitive sensor can include a hydrogel portion that is chemically configured to vary its displacement volume according to changes in concentration of an analyte in the surrounding area. Hydrogels sensitive to analytes have been described, for instance in U.S. Pat. No. 6,751,491 to Lew, et al., U.S. Pat. No. 6,835,553 to In Suk Han, et al., and U.S. Patent Application Publication No. 2009/0170209 to Machauf, et al., all of which are incorporated herein by reference. As a component of a sensor, the hydrogel can be disposed within a housing as described previously. The housing at least in the area of the hydrogel can include a semipermeable membrane to prevent contact between the surrounding environment, while allowing the analyte to pass through the membrane and interact with the analyte-sensitive hydrogel. The housing and membrane may also be configured to prevent surrounding tissue from mechanically pressing on the hydrogel.

An analyte-sensitive hydrogel may include any analyte-sensitive material that can directly or indirectly modify the displacement volume of the hydrogel in response to a change in analyte concentration. For example, the analyte-sensitive material can directly bond with the analyte to modify the displacement volume of the hydrogel. Alternatively, the analyte-sensitive material can catalyze a reaction of the analyte and the reaction product can directly or indirectly modify the displacement volume of the hydrogel.

Figure 23:
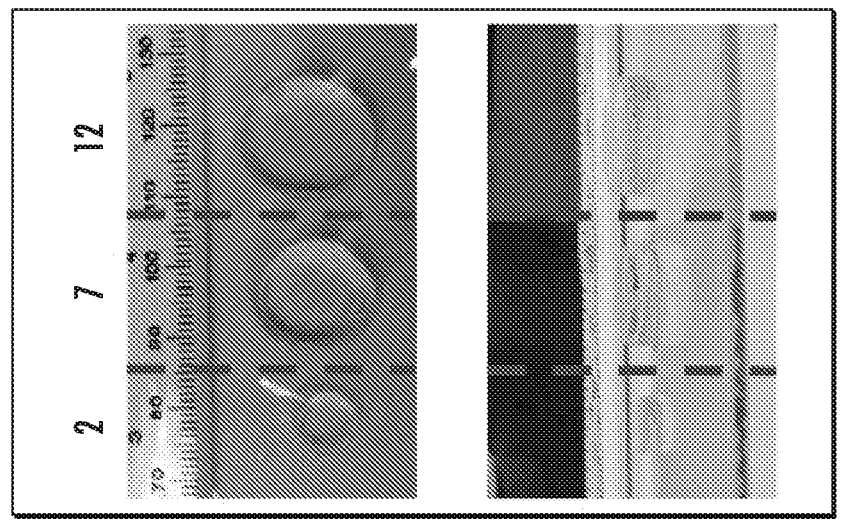
FIG. 23 illustrates top views (left) and side views (right) of an increasingly swollen hydrogel indicator as may be utilized in a chemical sensor as described herein.
Figure 24:
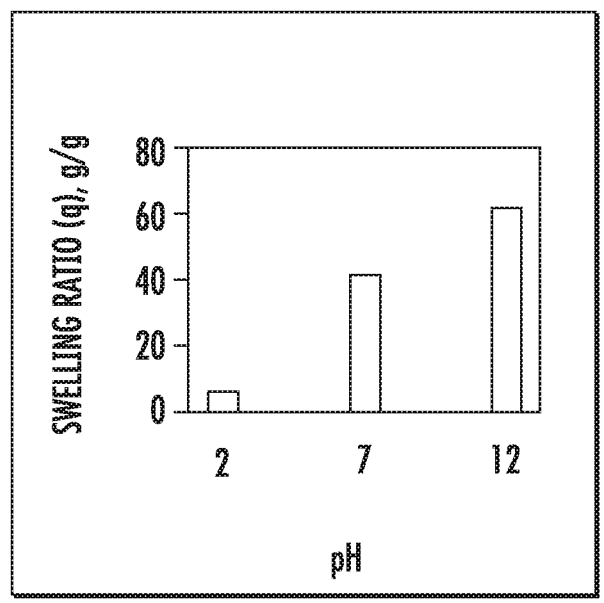
FIG. 24 graphically illustrates the swelling ratio of a hydrogel with pH.

By way of example and without limitation, in one embodiment, an analyte-sensitive material can be immobilized within a pH-sensitive hydrogel. As utilized herein, the term 'pH-sensitive hydrogel' refers generally to a hydrogel modified to contain pendant charged groups on polymers of the hydrogel in proportions that produce an overall acidic or basic environment in the fluid within the gel. An analyte-sensitive material present in the hydrogel can bind to the targeted analyte or catalyze a reaction of the targeted analyte and thereby provide a charged product within the hydrogel. The charged product generated by activity of the analyte-sensitive material can cause the hydrogel to change its displacement volume (swell or shrink). For example, FIG. 23 presents top views (left) and side views (right) of a pH sensitive hydrogel made from polyacrylic acid in increasingly basic environments. FIG. 24 graphically illustrates the swelling ratio of the hydrogel of FIG. 23 with increasing pH.

A pH-sensitive hydrogel can include a copolymer synthesized from various types of methacrylate-derived monomers by free radical solution polymerization as are known in the art. Such copolymers can be relatively tough, flexible polymers that are highly biocompatible and inert yet non-degradable in vivo. Synthesis conditions for pH-sensitive hydrogels have been well established. In one particular embodiment acrylamide or dimethylacrylamide can be utilized as a polymer backbone, sodium acrylate as a pH-sensitive pendant group, and N,N'-methylene-bis-acrylamide as the cross linker. To obtain pH sensitive hydrogel copolymers with desired properties, the ratios of the monomers and cross-linker can be varied as is known in the art.

The targeted analyte can include one or more compounds the presence of which in the local area of an orthopedic implant can indicate infection. For instance, the analyte can include a pathogen or a determinant of a pathogen that can be, e.g. an endotoxin or exotoxin of the pathogen or a compound present in the local area due to an infection response of the host. Analytes of interest can include, without limitation, hydrogen ions (e.g., pH), quorum sensing molecules, glucose, lactic acid, carbon dioxide, proteins, proteases, antibiotics, drugs, etc.

In one particular embodiment, the targeted analyte of a sensor can be glucose, which can provide an indication of infection from a broad range of causative agents. Even at early stages, the presence of infection is generally accompanied by an inflammatory state. Cytokines released during inflammation can affect glucose metabolism directly or indirectly by augmenting glucoregulatory hormone secretion and curtailing insulin release. In particular, glucose can be shunted away from its normal sites of utilization to sites that assist in overcoming infection, and as such increased levels of glucose in a local area can be an excellent broad-spectrum indicator of early-stage infection in the area.

One such glucose-sensitive chemical sensor can include an immobilized glucose oxidase that can detect the presence of glucose via the conversion of glucose to gluconic acid by the enzyme. The rate of gluconic acid formation is proportional to the glucose concentration in the hydrogel at the reaction location. A change in glucose concentration in the fluid surrounding the hydrogel can lead to a change in the pH value within the hydrogel due to the glucose oxidase-catalyzed production of gluconic acid. In particular, the gluconic acid product can protonate pH-sensitive pendant groups in the hydrogel and causes the hydrogel to swell or shrink, depending on the nature of the pendant groups. If the hydrogel contains basic pendant groups such as diethylaminoethyl methacrylate, it will swell when pH decreases. If it contains acidic pendant groups such as acrylic acid (AA), the hydrogel will shrink when pH decreases.

In another embodiment, an analyte-sensitive material can directly interact with the targeted analyte. For instance, a hydrogel can include analyte binding molecules and upon binding, the hydrogel can exhibit a change in volume due to steric changes within the hydrogel or the presence of charge groups on the bound analyte (e.g., in the case of a pH sensitive hydrogel).

In yet another embodiment, an analyte-sensitive hydrogel can include analyte binding molecules and analyte analogue molecules immobilized therein, optionally in conjunction with charged pendant groups on the hydrogel polymer. In the absence of free analyte, the immobilized analyte binding molecules can bind to the immobilized analyte analogue molecules, forming what are in effect crosslinks within the hydrogel (generally non-covalent crosslinks). As free analyte in the local area interacts with the hydrogel, binding competition can displace immobilized analyte analogue molecules with free analyte molecules, thus reducing the number of crosslinks. This reduction in crosslinking causes swelling of the hydrogel. This type of sensitive hydrogel is based on a competitive mechanism and does not require oxygen-consuming enzymatic reactions.

In one embodiment, an analyte binding hydrogel can contain immobilized phenylboronic acid or another glucose binding molecule that can be covalently bonded to the hydrogel polymer, for instance via diols on the hydrogel polymer. For instance, a hydrogel can include one or more polyols such as poly(vinyl alcohol) (PVA), with other pendant groups as necessary to achieve the desired sensitivity, response, and durability. As discussed above, an analyte binding hydrogel can optionally include analyte analogue molecules, such as a D-sugar or other carbohydrate that can bind the glucose binding molecule with a non-covalent bond. The volume of this hydrogel can change in the presence of free glucose due to a competitive binding effect of the free glucose with the glucose binding molecule in place of the glucose analogue molecule. When glucose concentration increases near the implant area, additional amounts of free glucose can diffuse into the hydrogel and displace the glucose analogue (e.g., a D-sugar) from the binding sites of the immobilized glucose binding molecule. This can reduce the hydrogel crosslink density, and thus the hydrogel can swell.

To produce a competitive binding glucose targeting hydrogel, glucose analogue molecule-conjugated and glucose binding molecule-conjugated vinyl monomers can be synthesized. These conjugated monomers can then be co-polymerized with cross linkers and either cationic or anionic monomers as discussed above. The cross linker introduces a small number of permanent crosslinks into the hydrogel in order to keep hydrogel integrity at all free glucose concentrations.

Examples of glucose binding molecules can include, without limitation, lectins (e.g., Con A, glucokinase, xylose isomerase, and isolactin I), glucose antibody, concanavalin A, boronic acid, thiols, cell membrane receptors, cytosol receptors, nuclear receptors, heparin, DNA, RNA, polylysine, polyarginine triazine dye, commassie blue, azure A, metal binding molecules including chelating agents, etc. Examples of glucose analogue molecules can include, without limitation, glucose antigen, glucose cofactor, glucose substrate, glucose inhibitor, D-sugar, carbohydrates, 1,2-cis-diol sugars, cysteine, metal ions (e.g., Ca, Mg, etc.), etc.

A sensor can also include a semi-permeable membrane that can protect the hydrogel such that analyte-containing body fluid is free to pass through the membrane and permeate the hydrogel. A membrane can generally have a thickness on the order of microns. In one embodiment, a membrane can be radiographically transparent. In addition, the membrane can be biocompatible and have sufficient stiffness to substantially prevent the hydrogel from swelling in undesirable directions and from escaping into the surrounding area.

In one embodiment, a semipermeable membrane can be permeable to the passage of the analyte and any other materials utilized in the sensing application (e.g., glucose, oxygen, carbon dioxide, lactic acid, gluconic acid, etc.) and can be totally or substantially impermeable to the passage of blood clots, cells, and non-analyte proteins. In addition, a semipermeable membrane can be an inert, nontoxic material that maintains its integrity when implanted in humans. A suitable biocompatible semipermeable material, to minimize immune reactions and to prevent protein and cell absorption, can be selected from the group of polymers including, without limitation, cellulose acetate, methyl cellulose, polyvinyl alcohol, polypropylene, HEMA, tetra-acrylated poly (ethylene glycol) (PEG), and/or polyurethane.

There is an extensive body of knowledge on developing stimuli-responsive gels for chemical sensors, actuators (e.g. artificial muscles), and drug release materials. For example, a partial review of stimuli responsive materials is given in Journal of Controlled Release 190 (2014) 337-351. Many methods are available to detect different types of analytes include coupling pH-responsive gels to enzymes that generate acidic products (e.g. glucose and oxygen can be detected by encapsulating glucose oxidase and catalase into a pH responsive gel to produce gluconic acid according to the concentration of glucose and oxygen present). Alternatively, molecular recognition interactions (e.g. antibody-antigen, lectin-carbohydrate, ionophore-ion, enzyme-substrate, DNA-complementary DNA, aptamer-substrate, etc.) can be used to affect gel swelling. The gel swelling can be measured based upon axial expansion, bending of a multi-layered structure with different expansion properties in the structure (e.g. in cantilever-based chemical sensors, and similar to the working of bimetallic thermal sensors/actuators and paper-based hygrometers). Multi-layered structures can be formed by bonding two or more structures together, or allowing particles to settle within a polymer, varying the amount of cross-linking in the top of a polymer film compared with the bottom, etc. Multiple sensors can be used to increase specificity and account for interactions between multiple variables. For example, the combination of a pH sensor and a separate glucose sensor with glucose oxidase can be used to account for how the ambient pH affects the glucose sensor in order to estimate the two analyte concentrations. In addition, measuring multiple analytes may be more indicative of pathology (e.g. infection) than a single analyte.

A chemical sensor can be affixed to an orthopedic implant, similar to strain sensors as discussed above but this is not a requirement of a chemical sensor, as the response of the chemical sensor does not depend upon the action of the implant or the bone. Accordingly, the indicator of the chemical sensor need not be directly or indirectly attached to the bone at any point, but should be implantable in the local area of the implant. As such, it may be convenient to locate a chemical sensor on the implant. Alternatively, a chemical sensor can be located directly on a bone or on another structure in the general area. In any case, a chemical sensor can be located such that it can be examined radiographically to determine the presence of an analyte in the local area of the implant. In one embodiment, the analyte-sensitive material can function as the radiographically discernable material. For instance, a sensor as illustrated in FIG. 9 can include an analyte-sensitive material in the reservoir 221 at the first end 226 of the indicator 22. Upon contact with the analyte, the analyte-sensitive material can swell and extend along the track 223 of the sensor. In this embodiment, the sensor 220 can be configured to permit expansion of the hydrogel in substantially only one dimension along the track 223. In order to be clearly discernable in the radiographic imaging, the track 223 can have a length that is greater than the width of the track, e.g., from about 5 to about 50 times the crosswise dimension(s). Upon interaction with the analyte and dimensional variation of the hydrogel held at the first end 226 of the indicator 222, the hydrogel can be forced along the track 223, and the motion of the indicator (e.g., the second end 227 of the hydrogel) can be discernable by radiographic imaging.

Figure 25:
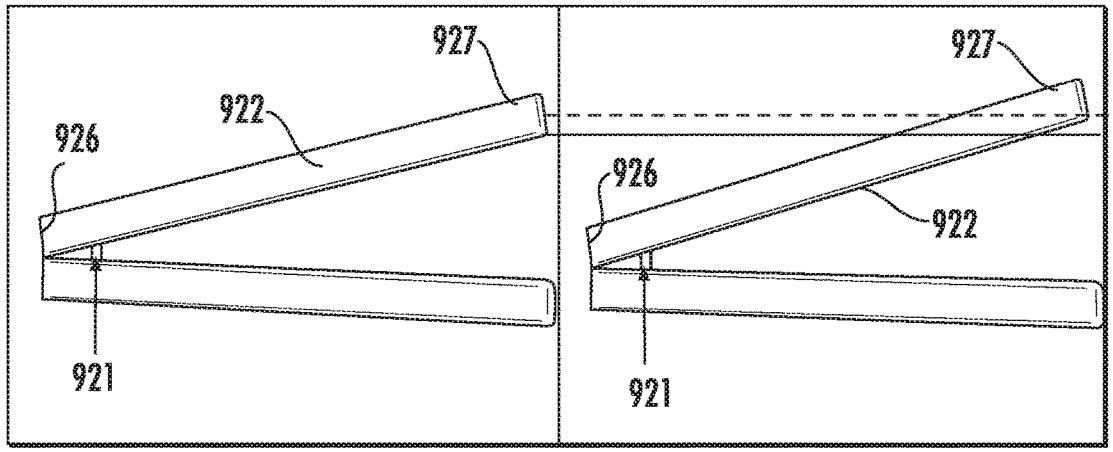
FIG. 25 illustrates a chemical sensor prior to (left) and following (right) swelling of a hydrogel indicator.

In another embodiment, the analyte-sensitive material can be in communication with a secondary component of the indicator that can amplify the volume variation of the analyte-sensitive material. For instance, and with reference to FIG. 25, a sensor 920 is illustrated that includes an analyte-sensitive hydrogel 921 held adjacent to a first end 926 of an indicator rod 922. In the left panel, the analyte-sensitive hydrogel is illustrated in a neutral condition, e.g., not in the presence of the analyte. Following contact with the analyte of interest, the hydrogel 921 can swell, which can cause the indicator rod 922 to rotate, elongate, or otherwise alter the location of the second end 927 of the indicator rod 922. The second end 927 of the indicator rod can be held in conjunction with a scale as discussed above, such that the location of the second end 927 with respect to the scale is radiographically discernible.

Figure 26:
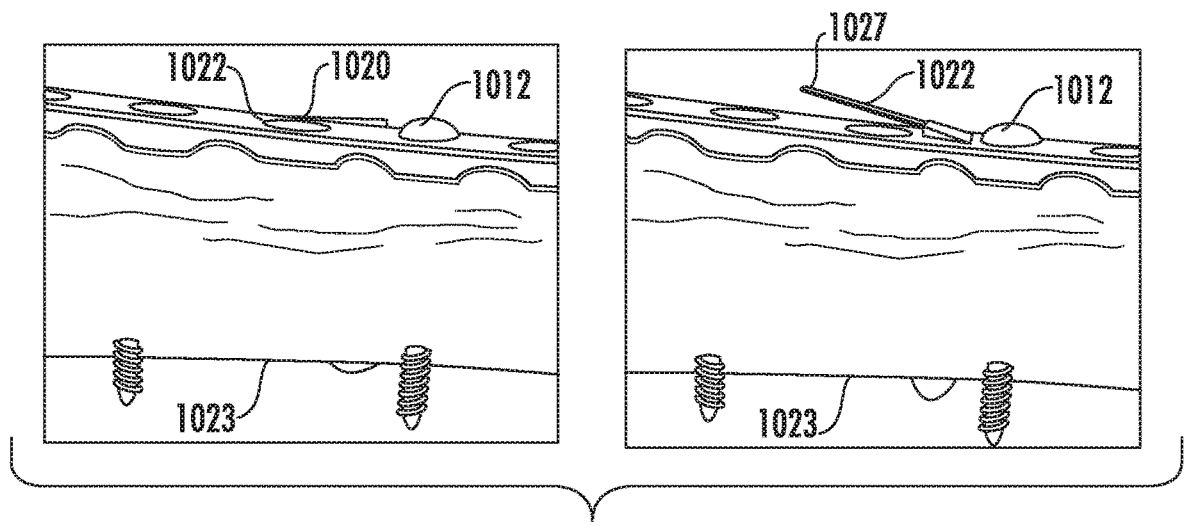
FIG. 26 illustrates another chemical sensor affixed to an orthopedic implant in the absence of swelling of the hydrogel indicator (left) and following swelling of the hydrogel indicator (right).

FIG. 26 illustrates a chemical sensor 1020 attached to a surface of an orthopedic implant 1012, which is in turn attached to a bone model 1023. The left panel illustrates the analyte-sensitive hydrogel (not visible in FIG. 22) prior to exposure to the analyte. In the right panel, the hydrogel has swollen due to exposure to the analyte, and the change in location of the second end 1027 of the indicator rod 1022 is clearly visible. When utilized in vivo, the second end 1027 of the indicator rod 1022 can be located in conjunction with a scale, as discussed previously, so as to quantify the distance moved by the second end 1027 of the indicator rod 1022. This distance can indicate the presence or concentration of the analyte in the area of the sensor 1022.

Figure 27:
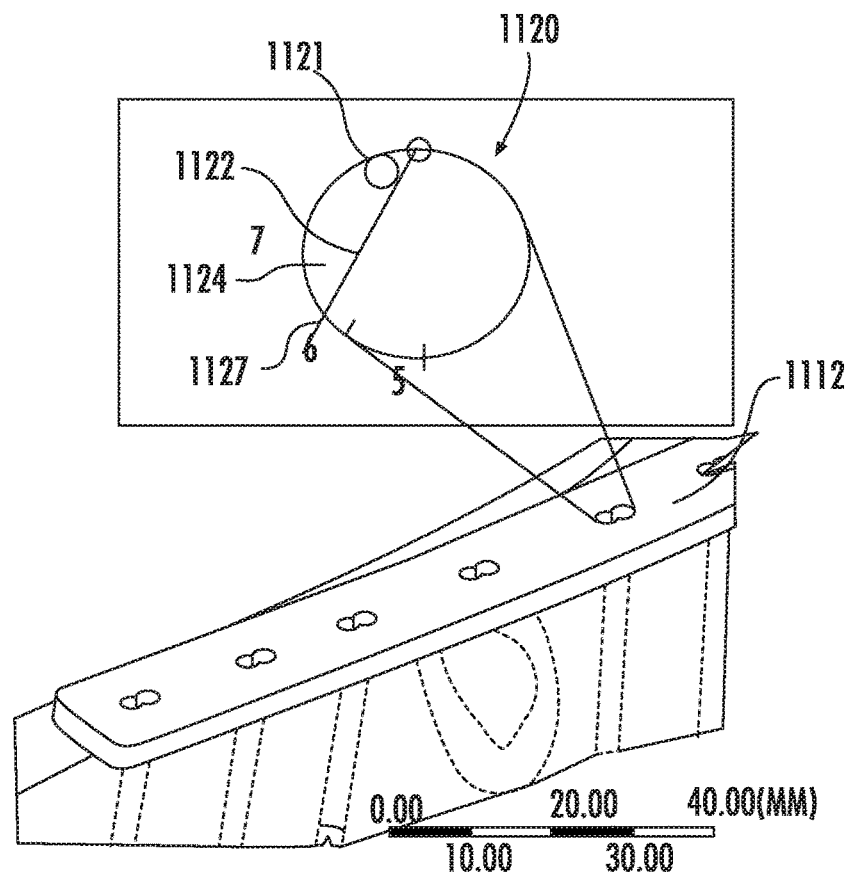
FIG. 27 illustrates a chemical sensor affixed to an orthopedic implant.

As with the strain sensors, a chemical sensor can be located at any convenient location in conjunction with an orthopedic implant in order that an end of the indicator and the scale are discernible without interfering with the function of the implant or causing undesirable irritation to surrounding tissue. For instance, in one embodiment illustrated in FIG. 27, a sensor 1120 can be located within an aperture (e.g., an unused screw hole) of an orthopedic implant. As can be seen, the sensor 1120 includes an analyte-sensitive material 1121 and an indicator rod 1122. In addition, the sensor 1120 includes a scale 1124 in the form of markings around the circumference of the sensor 1120. Upon interaction with an analyte, the analyte-sensitive material 1121 can exhibit a dimensional change that can be translated to the indicator rod 1122. Upon radiographic imaging of the sensor, the location of the movable end 1127 of the indicator rod 1122 with respect to the scale 1124 can be determined, and this can provide information regarding the presence or concentration of the analyte in the local area of the orthopedic implant 1122.

The analyte-sensitive component of an indicator, e.g., an analyte-sensitive hydrogel, can be a single piece of material or can include a plurality of pieces of material. In addition, multiple pieces of analyte-sensitive material can exhibit a detectable response in the presence of the same or different analytes.

Figure 28:
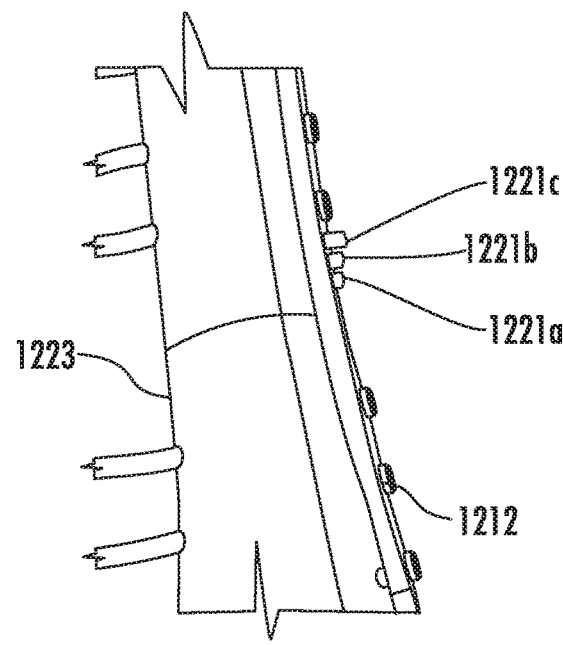
FIG. 28 illustrates a chemical sensor capable of determining presence of multiple analytes.

FIG. 28 illustrates an embodiment of a chemical sensor that includes multiple segments of analyte-sensitive material 1221a, 1221b, and 1221c affixed to an orthopedic implant 1212 that, in turn is affixed to a bone 1223. The different segments of analyte-sensitive materials can provide different functions. For instance, one of the segments 1221a can be utilized as the scale. For instance segment 1221a can be a non-reactive hydrogel segment that is not sensitive to the presence of the analyte. A second segment 1221b can be sensitive to a particular analyte, e.g., glucose. For instance, the second segment 1221b can include specific analyte binding molecules incorporated therein that are specific for an analyte of interest. A third segment 1221c can be sensitive to a different specific analyte or can exhibit a more general response. For instance, the third segment 1221c can exhibit a dimensional variation in response to a pH change, independent of the cause of the pH change. During use, a dimension (e.g., height) of the analyte-sensitive segments 1221b, 1221c, can be compared to one another as well as to the scale segment 1221a to provide information regarding the presence or concentration of one or more analytes of interest.

Of course, additional sensitive materials specific to other analytes of interest can also be included in a chemical sensor, and a sensor is in no way intended to be limited to determination of the presence or concentration of any particular number of analytes. Moreover, multiple sensors including any combination of chemical and strain sensors can be used in an area. For instance, a joint, bone, or general area including one or more orthopedic tissues can include one or more strain sensors optionally in conjunction with one or more chemical sensors.

The present disclosure may be better understood with reference to the Examples set forth below Example 1

Figure 29:
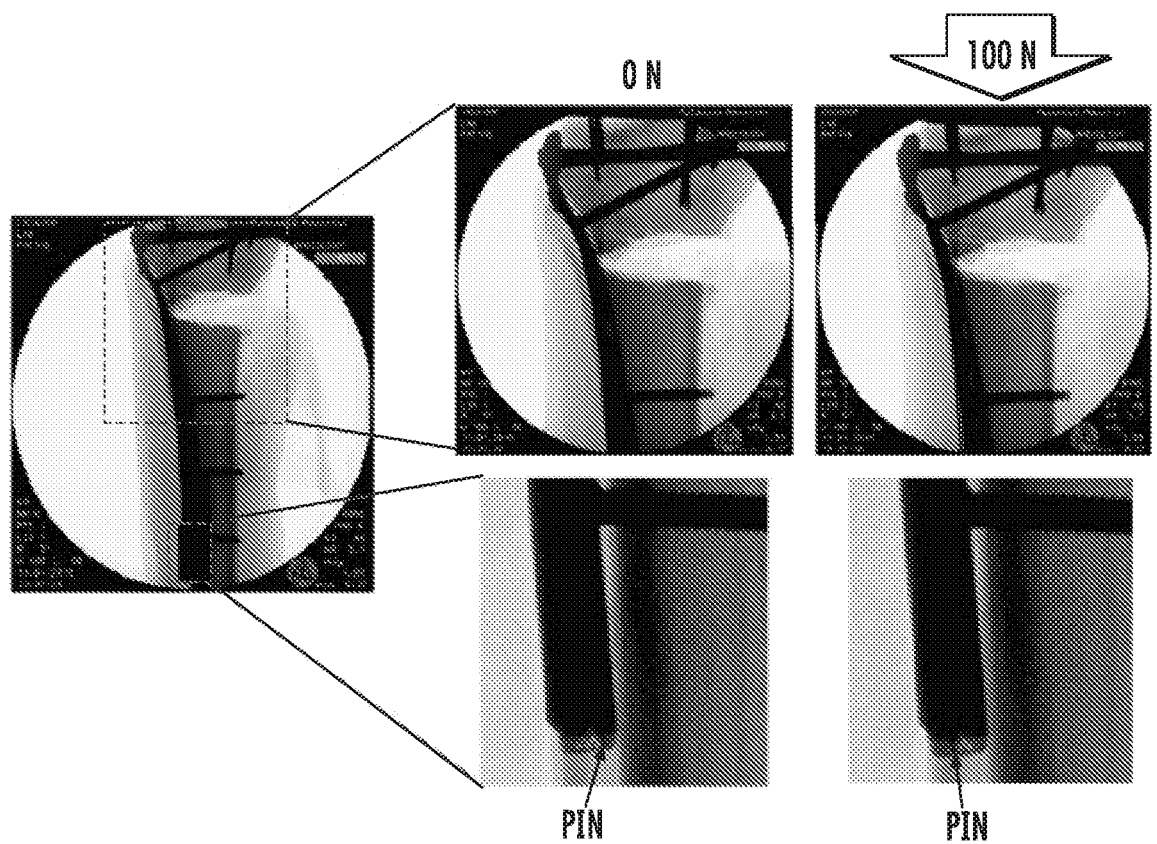
FIG. 29 illustrates a plated tibia fracture with a magnified view of a sensor as described herein under no load and under a 100 N load.

A lever-type strain sensor was formed and attached to a human cadaver tibia. The scale included 0.4 mm holes formed in a tungsten plate and separated from one another by a distance of 0.75 mm. A tungsten rod was used as the indicator. The rod was 0.89 mm in diameter and 80 mm in length. Using a C-arm X-ray system, the position of the tungsten rod relative to the 0.4 cm hole scale was evident and movement was clearly observed; while no motion was evident for loading an intact human cadaver tibia. The introduction of an unstable fracture caused significant motion under axial loading of ½ body weight (FIG. 29). These results qualitatively agreed with the FEA simulation described above (although the cadaver experiments were more sensitive as a longer dial arm was used). The sensor did not affect plate mechanical properties. The sensor could detect changes in pretension (e.g. from subsidence), though the main purpose was to measure stiffness by detecting changes in position during stance loading. This easily read sensor moved four holes under a load of only 100 N, with readings repeatable under cyclic loading (FIG. 29 at right).

FIG. 30 at A illustrates a computer simulated strain in callus for a 400 N axial compression load (½ body weight) on a plated tibia with a 1 cm tibial osteotomy and a spacer with varying stiffness relative to intact bone (darkness indicates the log of strain). At B is graphically shown a comparison of pin displacement with maximum callus strain. The non-zero y-intercept at B indicates some displacement when the callus is fully healed because the device reads the bending of the whole bone construct. As shown at B, movement of the second end was detected at about 0.5 mm at a maximum callus strain of about 1.5% (150 μm for a 1 cm fracture gap), a likely safe level for weight bearing. Simulations with 20 N kicking/ground reaction forces showed an essentially identical displacement at a 400 N axial compression.

Additional response data for a strain sensor are graphically presented in FIG. 31 including pin displacement (mm) with axial compression load (N) (left), pin displacement (mm) with callus stiffness as a percentage of intact bone (400 N axial compression load, BW/2) (center), and pin displacement under a bending load (mm) vs. pin displacement under an axial compression (mm) for a 400 N compression vs. a 35 N bending load with various fracture callus stiffness (right).

Example 2

A 1 mm tungsten rod was press fit into a threaded stainless steel cylinder. This threaded piece was then screwed into a titanium dynamic hip screw (Narang Inc) (FIG. 22 at (a)), and imaged using projection radiography (FIG. 22 at (d)). The position of the pin could be easily discerned through the titanium screw using standard X-ray radiography with 82 kV applied to the X-ray tube (FIG. 22 at (d)). Generally, higher energy X-rays were able to penetrate more deeply through titanium or steel. The experiment was therefore repeated with a stainless steel screw, using a tube voltage of 100 kV, and the position could be determined via X-ray. Under bending loads, the pin moves relative to the screw providing a readout for amount of bending (FIG. 22 at (e)).

Example 3

To synthesize a chemical sensor including a pH responsive polyacrylic gel, an aqueous solution was prepared by mixing the monomer, acrylic acid (AAc) (2.0 M), a chemical cross-linker, methylene bis acrylamide (MBAAm) (2.0 mol %), and a thermal initiator, ammonium per sulfate (APS) (0.15 mol %) together (the amount in mol % is related to the AAc monomer concentration). After homogeneous mixing, the precursor solution was poured into a reaction cell consisting of a ~1.0 mm thick rectangular silicone rubber frame sandwiched between a pair of parallel flint glass plates. Polymerization reaction was effected at the temperature nearly 65° C. under nitrogen atmosphere in a vacuum oven. After prolonged, ~6 hr. thermal polymerization, the plate-like gel (about 40×40×1.0 mm3) was obtained and carefully removed from the glass reaction cell and cut into specific dimensions (a disk of about 5.0 mm diameter and 2.0 mm thickness) using a metallic cutter. Then, the gels were immersed in water for spontaneous swelling. Water was changed every 24 hr. at least for 3 days to remove all unreacted monomers in the gel. Finally swollen disk-gel pieces were carefully incubated in a sealable container to carry out an experiment for measuring swelling induced strain of the gel.

A gel-sensor placed in the built-in screw hole of an implanted orthopedic plate demonstrated abrupt changes in volume due to the occurrence of swelling and de-swelling when the appropriate pH buffer was used as stimuli. A small piece of water (pH~5.5) swollen gel (about 2.0 mm×2.0 mm×2.0 mm) was placed in the hole of an orthopedic implant fixed on a human bone. A thin (0.5 mm radius) tungsten rod was attached on the top of the implant such a way that the rod touched the surface of the swellable gel and could rotate like a dial when the gel volume changes due to swelling/deswelling. The set up and results of this experiment are presented in FIG. 32. In this figure, the x-ray images demonstrate the position of free-end of the tungsten dial before and after the addition of biological simulant buffer (enlarged X-ray images on the right shows clearly what was being occurred in the left images). Prior to start swelling of the gel-sensor the rod-end was gently touched the plate surface, the position of the rod-end, therefore, was settled in hole #1. When the spontaneous swelling was commenced by injecting high pH buffer (~7.0), mass/volume of the gel-sensor increased significantly, the tungsten dial, therefore, was displaced which is evidenced by clear visualization of the rod-end at the hole #4 or somewhere between #3, and #4. Later, when the buffer was changed into low pH (~4.0) to occur de-swelling the rod-end took position back to the hole #1. FIG. 33 illustrates the repeatability of the sensor response through multiple cycles of pH. This simple experiment was a clear exhibition of the capability of the gel-sensor for internal biomedical devices.

Example 4

An orthopedic surgeon fixed an implant on a cadaver tibia and following attached a gel sensor utilizing a pH sensitive gel as described above in the implant (FIG. 34 at (a)). FIG. 34 at (b) presents a schematic diagram of the gel sensor during use. X-ray images enlarged in FIG. 34 at (c) illustrate the tungsten dial and the relative motion of the indicator when at high and low pH.

Example 5

The concentrations of reagents of a pH sensitive hydrogel were varied to provide a thin hydrogel (200 um thick) with fast response rate. In addition to the reagents described above, the gel included n-octyl acrylate to provide sensitivity at higher pH than was observed using only acrylic acid. After synthesis, it was verified that the sensor shrunk in respond to acidic products from bacterial growth and re-swelled in response to incubation in pH 7.4 buffer.

To synthesize the pH sensitive hydrogel film, a solution was prepared by combining the monomers, acrylic acid (AAc), and n-octyl acrylate ($C_8$-A), the chemical cross-linker, poly(ethylene glycol) diacrylate 700 (PEGDA), and the photo-initiator, 2-oxoglutaric acid (OGAc). These reagents were mixed together in the following ratios: AAc+ $C_8$-A+PEGDA700+OGAc (10+5+1+0.1) (wt/wt %) in N, N-dimethyl formamide (DMF). After homogeneous mixing, the precursor solution was degassed by $N_2$ and was then poured into a simple reaction cell, where a rectangular frame of 100 μm thick silicone rubber was sandwiched between a pair of parallel flint glass plates. The spacer and glass plates were cleaned very carefully before use. Under an inert nitrogen atmosphere maintained in a glove box (Cleatech), a photo-polymerization reaction was performed by using UV lamps (360 nm) irradiation at a distance 10 cm from the both sides of the reaction cell at the temperature nearly 30-35° C. After a prolonged ~6 hr. polymerization, a piece of hydrogel film (size: about 40×40×0.1 mm$^3$) was obtained and was removed carefully from the customized glass reaction cell. Following, the gel pieces were immersed in sufficient water for spontaneous swelling. Water was changed every 24 hrs. for at least 3 days, to remove all the un-reacted molecules in the hydrogel. Water swollen gels were transferred and finally incubated into a phosphate buffer saline PBS (1×) at pH~7.4. To implement as sensor, such PBS swollen hydrogel film are cut into a disk-shaped using a metallic hole-punch (about 12.0 mm diameter and 0.2 mm thickness in this study).

The hydrogel-sensor, swollen in PBS 1× (diameter of ~12.0 mm, and thickness of ~0.2 mm) was sterilized by rinsing with ethanol-water mixture (70-30% ratio), exposed under UV, and finally incubated again in PBS 1× at 37° C. Next, a bacteria (*Staphylococcus epidermis*, ATCC 35984) culturing media was prepared from sterilized tryptic soy broth (TSB) which contains 1.0 wt/vol % glucose. Following this TSB media (~25 mL, and pH~7.0) was mixed with some extent of bacteria and incubated in 37° C. prior to use.

A piece of the hydrogel-sensor (diameter of ~12.0 mm, and thickness of ~0.2 mm) was carefully taken out from PBS and was directly dipped into the bacterial suspension in TSB and the culture was kept in the incubator. After 24 and 48 hours, the culture was taken out, pH of the media was measured and image of the hydrogel was recorded to determine the change in size/volume. One hydrogel sample was added to each centrifuge tube. After collecting the 48 hour data point, the hydrogel-sensor was returned to the PBS 1× solution (pH~7.4) at 37° C. and its restorable size was recorded.

The initial pH of the TSB media was 7.1, and the initial diameter of the hydrogel was 12.17 mm. After 24 hours, the pH was reduced to 4.68 due to bacterial growth and the hydrogel diameter was reduced to 6.35 mm. After 48 hours, the pH increased to 4.73 and the concomitant hydrogel diameter was measured 6.39 mm. After the completion of 48 hour incubation period, the hydrogel-sensor was rinsed in the PBS 1× of pH~7.4 three times, and allowed to expand due to swelling. After a short while (~20-25 mins) the diameter of the hydrogel-sensor was recovered into 11.76 mm which is 0.41 mm less than the diameter of virgin hydrogel-sensor.

While certain embodiments of the disclosed subject matter have been described using specific terms, such description is for illustrative purposes only, and it is to be understood that changes and variations may be made without departing from the spirit or scope of the subject matter.

What is claimed is:

1. An implantable strain sensor comprising an indicator, the indicator including a first end and a second end, the first end being configured for direct or indirect fixation to an orthopedic implant, the second end comprising a first radiographically opaque material, the sensor further comprising a scale comprising a second radiographically opaque material, the scale being located in conjunction with the second end, wherein the strain sensor is a passive sensor such that a location of the second end with respect to the scale is discernible via X-ray imaging with no active interrogation of the first or second radiographically opaque materials.

2. The implantable strain sensor of claim 1, further comprising a housing, the housing containing the indicator and the scale.

3. The implantable strain sensor of claim 1, wherein the indicator comprises an elongated rod or an extendable material.

4. The implantable strain sensor of claim 1, the scale comprising multiple features, each feature having a cross sectional dimension of from about 0.1 millimeters to about 1 millimeter.

5. The implantable strain sensor of claim 1, the second end having a width of from about 0.1 millimeters to about 1 millimeter.

6. An orthopedic implant comprising the implantable strain sensor of claim 1 attached thereto.

7. The orthopedic implant of claim 6, wherein the strain sensor is attached to an exterior surface of the orthopedic implant or is within a cannula of the orthopedic implant.

8. The implantable strain sensor of claim 1, wherein the radiographically opaque material comprises tungsten, stainless steel, tantalum, mercury, gallium, galistan, a rare earth nitrate, gold, bismuth, gadolinium oxysulfide, polydimethyl siloxane, or an acrylic elastomer.

9. A method for determining health of orthopedic tissue comprising:
placing orthopedic tissue under a load, the orthopedic tissue having affixed thereto an orthopedic implant and a strain sensor, the strain sensor comprising an indicator, the indicator including a first end and a second end, the first end being directly or indirectly attached to the orthopedic implant, the second end comprising a first radiographically opaque material, the sensor further comprising a scale, the scale comprising a second radiographically opaque material;
examining the orthopedic tissue via an X-ray imaging process while the orthopedic tissue is under the load, the examination comprising no active interrogation of the first or second radiographically opaque materials, the X-ray imaging providing one or more images of the scale and the second end of the indicator.

10. The method of claim 9, further comprising examining the orthopedic tissue via the X-ray imaging process while the orthopedic tissue is under no load, and comparing the examination results.

11. An implantable chemical sensor comprising an indicator, the indicator including an analyte-sensitive material and a radiographically opaque component configured for movement in response to a dimensional change in the analyte-sensitive material, wherein the chemical sensor is a passive sensor such that the radiographically opaque component is discernible via X-ray imaging with no active interrogation of the radiographically opaque component.

12. The implantable chemical sensor of claim 11, wherein the analyte-sensitive material comprises an analyte-sensitive hydrogel or comprises a pH sensitive hydrogel.

13. The implantable chemical sensor of claim 11, wherein the radiographically opaque component is an end of the analyte-sensitive material.

14. The implantable chemical sensor of claim 11, wherein the radiographically opaque component is confined within a track.

15. The implantable chemical sensor of claim 11, the indicator further comprising an indicator component in mechanical communication with the analyte-sensitive material, the indicator component including the radiographically opaque component.

16. The implantable chemical sensor of claim 11, the analyte-sensitive material comprising a binding molecule or an analogue molecule for the analyte.

17. The implantable chemical sensor of claim 11, further comprising a scale, the scale being located in conjunction with the radiographically opaque component such that the location of the radiographically opaque component with respect to the scale is discernable via X-ray imaging with no active interrogation of the radiographically opaque component.

18. The implantable chemical sensor of claim 11, further comprising a semi-permeable membrane.

19. The implantable chemical sensor of claim 11, comprising multiple analyte-sensitive materials each sensitive to at least one analyte.

20. The implantable chemical sensor of claim 11, wherein the analyte-sensitive material is sensitive to glucose.

21. An orthopedic implant comprising the implantable chemical sensor of claim 11.

\* \* \* \* \*